(12) United States Patent
Kasischke et al.

(10) Patent No.: US 11,734,915 B2
(45) Date of Patent: Aug. 22, 2023

(54) AUTOMATED AND ASSISTED IDENTIFICATION OF STROKE USING FEATURE-BASED BRAIN IMAGING

(71) Applicant: University of South Florida, Tampa, FL (US)

(72) Inventors: Karl A. Kasischke, Riverview, FL (US); William Scott Burgin, Tampa, FL (US)

(73) Assignee: University of South Florida, Tampa, FL (US)

( * ) Notice: Subject to any disclaimer, the term of this patent is extended or adjusted under 35 U.S.C. 154(b) by 0 days.

(21) Appl. No.: 18/017,144

(22) PCT Filed: Aug. 23, 2021

(86) PCT No.: PCT/US2021/047102
§ 371 (c)(1),
(2) Date: Jan. 20, 2023

(87) PCT Pub. No.: WO2022/046612
PCT Pub. Date: Mar. 3, 2022

(65) Prior Publication Data
US 2023/0215153 A1    Jul. 6, 2023

Related U.S. Application Data

(60) Provisional application No. 63/069,684, filed on Aug. 24, 2020.

(51) Int. Cl.
*G06V 10/776* (2022.01)
*G06T 7/00* (2017.01)
(Continued)

(52) U.S. Cl.
CPC .......... *G06V 10/776* (2022.01); *G06T 7/0012* (2013.01); *G06T 19/20* (2013.01);
(Continued)

(58) Field of Classification Search
CPC .. G06V 10/776; G06V 10/25; G06V 10/7715; G06V 20/64; G06V 10/26;
(Continued)

(56) References Cited

U.S. PATENT DOCUMENTS

2009/0034812 A1* 2/2009 Nowinski ............... G06T 19/00
382/131
2013/0303900 A1* 11/2013 Nowinski .............. A61B 6/504
600/425
(Continued)

FOREIGN PATENT DOCUMENTS

WO    WO 2017/106645    6/2017
WO    WO 2020/033566    2/2020

OTHER PUBLICATIONS

Cardoso et al., "Geodesic information flows: spatially-variant graphs and their application to segmentation and fusion," IEEE transactions on medical imaging, Apr. 14, 2015, 34(9):1976-1988.
(Continued)

*Primary Examiner* — Vu Le
*Assistant Examiner* — Winta Gebreslassie

(57) ABSTRACT

Provided herein are systems and methods for automated identification of volumes of interest in volumetric brain images using artificial intelligence (AI) enhanced imaging to diagnose and treat acute stroke. The methods can include receiving image data of a brain having header data and voxel values that represent an interruption in blood supply of the brain when imaged, extracting the header data from the image data, populating an array of cells with the voxel values, applying a segmenting analysis to the array to generate a segmented array, applying a morphological neighborhood analysis to the segmented array to generate a features relationship array, where the features relationship array includes features of interest in the brain indicative of stroke, identifying three-dimensional (3D) connected vol- (Continued)

umes of interest in the features relationship array, and generating output, for display at a user device, indicating the identified 3D volumes of interest.

20 Claims, 8 Drawing Sheets
(3 of 8 Drawing Sheet(s) Filed in Color)

(51) Int. Cl.
*G06V 20/64* (2022.01)
*G06V 10/26* (2022.01)
*G06V 10/774* (2022.01)
*G06V 10/77* (2022.01)
*G06V 10/25* (2022.01)
*G06T 19/20* (2011.01)

(52) U.S. Cl.
CPC .............. *G06V 10/25* (2022.01); *G06V 10/26* (2022.01); *G06V 10/774* (2022.01); *G06V 10/7715* (2022.01); *G06V 20/64* (2022.01); *G06T 2207/10081* (2013.01); *G06T 2207/10088* (2013.01); *G06T 2207/20036* (2013.01); *G06T 2207/30016* (2013.01); *G06T 2207/30104* (2013.01); *G06T 2210/41* (2013.01); *G06T 2219/2012* (2013.01)

(58) Field of Classification Search
CPC ..... G06V 10/774; G06T 7/0012; G06T 19/20; G06T 2207/10081; G06T 2207/10088; G06T 2207/20036; G06T 2207/30016; G06T 2207/30104; G06T 2210/41; G06T 2219/2012
See application file for complete search history.

(56) References Cited

U.S. PATENT DOCUMENTS

| 2020/0074214 | A1 | 3/2020 | Boespflug et al. |
| 2022/0092772 | A1* | 3/2022 | Yuh .......................... G06T 7/11 |
| 2022/0198662 | A1* | 6/2022 | Ay .......................... A61B 5/742 |

OTHER PUBLICATIONS

International Search Report and Written Opinion in International Appln. No. PCT/US2021/047102, dated Jan. 5, 2022, 15 pages.
Saha et al., "Multiscale opening of conjoined fuzzy objects: theory and applications," IEEE Transactions on Fuzzy Systems, Nov. 20, 2015, 24(5): Abstract 9 pages.

* cited by examiner

AUTOMATED AND ASSISTED IDENTIFICATION OF STROKE USING FEATURE-BASED BRAIN IMAGING

CROSS-REFERENCE TO RELATED APPLICATIONS

This application is a U.S. National Phase Application of International Application No. PCT/US2021/047102, filed on Aug. 23, 2021, which claims priority to U.S. Provisional Patent Application No. 63/069,684, filed on Aug. 24, 2020, the content of both of which are incorporated by reference in their entirety.

TECHNICAL FIELD

This document generally relates to identifying strokes from brain image data.

BACKGROUND

Stroke is a major cause of disability in the United States. Stroke outcomes differ depending on where and how large the stroke event is. Acute ischemic strokes present with multiple restricted diffusion lesions scattered throughout a brain parenchyma, particularly embolic and watershed infarcts. The morphological variety and complexity of such infarcts can be high in terms of their potential number, shape, volume, and spatial distribution. Such infarcts can impose varying burdens and variabilities on a subject who experiences the stroke event.

SUMMARY

This document generally describes using artificial intelligence (AI) based approaches, such as machine learning algorithms, techniques, and models, to diagnose stroke events, such as acute stroke. The disclosed technology provides a semi-automatic tool that employs AI-based algorithms to present users, such as doctors, researchers, and other medical professionals, with validated and mapped brain stroke imagery. The disclosed technology can triage three-dimensional regions of interest in brain image data and provide quantitative measures about the brain (e.g., number of strokes, size of stroke volumes, distribution of stroke volumes in a brain, etc.) to help the users make informed, accurate, and quick decisions about stroke etiology, diagnosis, and treatment. The AI-based techniques described herein can provide for more accurate detection of stroke events from image data, including but not limited to Magnetic Resonance Imaging (MM), computed tomography (CT). Performing the described semi-automatic AI-based techniques can expand on the applicability and effectiveness of different image data by further enhancing clinical decisions through more advanced image analysis, presentation, and interpretation. A clinician or other relevant user can use the disclosed technology to more accurately and easily diagnose a subject's brain, stroke condition, and/or develop appropriate treatment.

The disclosed techniques therefore provide an AI-guided approach using high-performance computing, for fast (e.g., minutes or seconds) and precise (e.g., sub-milliliter) detection and quantification of infarcted brain volume(s), regardless of size and morphology, of the subject. This approach can employ processing and analyzing original DICOM data (or other image data) via filtering, segmentation, and morphological neighborhood operations to identify and triage three-dimensional (3D) connected volumes of interest that can represent ischemic stroke or other stroke events. The disclosed technology can provide for immediate measurement of absolute (in ml) and relative (in terms of % of total brain volume) infarct burdens of complex strokes on initial imaging data, which can otherwise be challenging to accomplish with existing technologies or manual human review of brain image data. Volumetric analysis of stroke can represent a critical future biomarker. The disclosed technology can therefore be implemented into clinical and research settings to guide clinical diagnoses, therapeutic decisions, and outcome predictions using AI-based volumetric analysis.

In addition to the embodiments of the attached claims and the embodiments described throughout this disclosure, the following numbered embodiments are also innovative.

Embodiment 1 is a system for automated identification of volumes of interest in brain image data, the system including one or more processors and computer memory storing instructions that, when executed by the processors, cause the processors to perform operations including: receiving image data of a brain having header data and voxel values, wherein the voxel values represent an interruption in blood supply of the brain when imaged, extracting the header data from the image data, populating an array of cells with the voxel values, applying a segmenting analysis to the array to generate a segmented array, applying a morphological neighborhood analysis to the segmented array to generate a features relationship array, wherein the features relationship array includes features of interest in the brain indicative of stroke, identifying three-dimensional (3D) connected volumes of interest in the features relationship array, and generating output, for display at a user device, indicating the identified 3D volumes of interest.

Embodiment 2 is the system of embodiment 1, wherein the 3D volumes of interest are at least one of watershed infarcts and embolic infarcts in the brain indicative of ischemic or hemorrhagic stroke.

Embodiment 3 is the system of any one of embodiments 1 through 2, wherein the image data of the brain is generated by at least one of computed tomography (CT) and Magnetic Resonance Imaging (MM).

Embodiment 4 is the system of any one of embodiments 1 through 3, wherein the image data of the brain includes time-series data of the brain generated as a contrast dye.

Embodiment 5 is the system of any one of embodiments 1 through 4, further comprising applying a filtering analysis to the array to generate a filtered array based on identifying a subset of the cells in the array to exclude from the filtered array, and removing the identified subset of the cells to generate the filtered array.

Embodiment 6 is the system of any one of embodiments 1 through 5, wherein applying the segmenting analysis comprises segmenting the cells of the array based on physiological structures of the brain.

Embodiment 7 is the system of any one of embodiments 1 through 6, wherein applying the morphological neighborhood analysis comprises identifying features of interest in the segmented array based on connectivity data amongst the cells in the segmented array.

Embodiment 8 is the system of any one of embodiments 1 through 7, wherein the operations further comprise storing, in a data store, the identified 3D volumes of interest.

Embodiment 9 is the system of any one of embodiments 1 through 8, wherein identifying three dimensional (3D) connected volumes of interest comprises counting voxel values within a predefined region of the image data to infer a volume of the brain, superimposing the identified 3D volumes of interest on the within the predefined region of the image data, and identifying relative infarct burden in percent of brain volume based on determining a ratio between the superimposed 3D volumes of interest and the inferred volume of the brain.

Embodiment 10 is the system of any one of embodiments 1 through 9, wherein generating output comprises generating coronal and sagittal views of the 3D volumes of interest in the brain image data.

Embodiment 11 is the system of any one of embodiments 1 through 10, wherein generating output comprises superimposing the 3D volumes of interest on the brain image data, and tinting the 3D volumes of interest in one or more indicia that is different than an indicia of the brain image data.

Embodiment 12 is the system of any one of embodiments 1 through 11, wherein tinting the 3D volumes of interest comprises tinting a first of the 3D volumes of interest in a first indicia based on determining that a volume of the first of the 3D volumes of interest is greater than a first threshold level, wherein the first indicia is a red color, tinting a second of the 3D volumes of interest in a second indicia based on determining that a volume of the second of the 3D volumes of interest is less than the first threshold level but greater than a second threshold level, wherein the second indicia is an orange color, tinting a third of the 3D volumes of interest in a third indicia based on determining that a volume of the third of the 3D volumes of interest is less than the second threshold level but greater than a third threshold level, wherein the third indicia is a yellow color, tinting a fourth of the 3D volumes of interest in a fourth indicia based on determining that a volume of the fourth of the 3D volumes of interest is less than the third threshold level but greater than a fourth threshold level, wherein the fourth indicia is a green color, tinting a fifth of the 3D volumes of interest in a fifth indicia based on determining that a volume of the fifth of the 3D volumes of interest is less than the fourth threshold level but greater than a fifth threshold level, wherein the fifth indicia is a blue color, and tinting a sixth of the 3D volumes of interest in a sixth indicia based on determining that a volume of the sixth of the 3D volumes of interest is less than a sixth threshold level, wherein the sixth indicia is a purple color.

Embodiment 13 is the system of any one of embodiments 1 through 12, wherein identifying three-dimensional (3D) connected volumes of interest in the features relationship array is based on applying one or more machine learning models that were trained using training datasets that include training brain image data labeled with areas of interest and training brain image data labeled with areas that are not of interest.

Embodiment 14 is a method for performing any one of the embodiments 1 through 13.

Moreover, provided herein are systems for automated identification of volumes of interest in volumetric brain images. The systems can include one or more processors, and computer memory storing instructions that, when executed by the processors, cause the processors to perform operations including receiving a volumetric image of a brain that includes header data and voxel values representing an interruption in the blood supply of the brain when imaged, extracting header data from the volumetric image, preprocessing the voxel values, populating an array of cells with the preprocessed voxel values, applying a filtering analysis to the array, applying a segmenting analysis to the array, applying a morphological neighborhood analysis to the array, and identifying three dimensional (3D) connected volumes of interest in the array.

The systems described herein can include one or more optional features. For example, the volumes of interest can represent ischemic or hemorrhagic stroke. In some implementations, the volumetric image can be generated by computed tomography (CT). The volumetric image can also be generated by Magnetic Resonance Imaging (MRI). As another example, the filtering analysis can identify some, but not all, of the cells to be excluded from future analysis. The segmenting analysis can include segmenting the cells of the array based on physiological structures of the brain as recorded in the array. In some implementations, the morphological neighborhood analysis can include feature detection to identify features of interest in the array based on connectivity of components represented in the array. In some implementations, the stroke can be an ischemic stroke. In some implementations, the stroke can be a hemorrhagic stroke.

As yet another example, the operations can further include displaying on a graphic user interface (GUI) the identified 3D connected volumes of interest. In some implementations, the operations further can include recording in a datastore the identified 3D connected volumes of interest. Identifying three dimensional (3D) connected volumes of interest in the array can include a confidence interval. In some implementations, populating an array of cells with the preprocessed voxel values can include populating an array in MATLAB.

Provided herein are also methods for automated identification of volumes of interest in a volumetric brain image, the method including receiving a volumetric image of a brain that has header data and voxel values representing an interruption in the blood supply of the brain when imaged, extracting header data from the volumetric image, preprocessing the voxel values, populating an array of cells with the preprocessed voxel values, applying a filtering analysis to the array; applying a segmenting analysis to the array, applying a morphological neighborhood analysis to the array, and identifying three dimensional (3D) connected volumes of interest in the array.

The method can include one or more optional features. For example, the volumes of interest can represent ischemic or hemorrhagic stroke. The volumetric image can be generated by computed tomography (CT). The volumetric image can be generated by Magnetic Resonance Imaging (MM). The method can be performed on one or more processors, and computer memory storing instructions that, when executed by the processors, can cause the processors to perform the method. In some implementations, the volumetric image can include time-series data generated as a contrast dye. In some implementations, the volumetric image can be a DICOM image.

Filtering analysis can include identifying some, but not all, of the cells to be excluded from future analysis. Segmenting analysis can include segmenting the cells of the array based on physiological structures of the brain as recorded in the array. Morphological neighborhood analysis can include feature detection to identify features of interest in the array based on connectivity of components represented in the array.

In some implementations, the stroke can be an ischemic stroke. The stroke can also be a hemorrhagic stroke.

The method can also include identifying multiple sets of three dimensional (3D) connected volumes of interest. The multiple sets of three dimensional (3D) connected volumes of interest can be taken over a period of time. The method can also include scoring volume-based stroke outcome. In some implementations, the method can include generating an outcome prediction. Identifying three dimensional (3D) connected volumes of interest in the array can include identifying measurement units. The measurement units can be milliliters. Identifying three dimensional (3D) connected volumes of interest in the array can also include identifying sub-milliliter volumes of interest. In some implementations, identifying three dimensional (3D) connected volumes of interest in the array can include identifying relative infarct volume. In some implementations, identifying three dimensional (3D) connected volumes of interest in the array can include identifying percentage of total brain volume.

The disclosed technology provides one or more of the following advantages. As an example, the disclosed technology provides for accurate stroke detection through analysis of robust sets of information and data. Information can be obtained and analyzed from examining a patient, collecting vitals such as heart rate, auscultate heart, and auscultate lungs, receiving information from other experts, analyzing vitals, lab reports, temperature, blood pressure, heart rate, respiratory rate, weight, glucose levels, INR, creatinine, Na, K, BUN, WBC, Hgb, Plt, reviewing and interpreting images from CT, CTA, CTP, and MRIs, and analyzing HPI, last known normal, onset of symptoms, pertinent past medical history, TPA exclusion criteria, medications, AP/AC doses, allergies, implants, and medical devices. The amount of data to gather, review, and interpret is overwhelming. Accordingly, the disclosed technology provides for synthesizing the abundance of data mentioned above to provide a user, such as a clinician, with more robust, automated, and accurate analysis into stroke diagnoses.

The disclosed technology also provides advanced image presentation and interpretation for users, such as clinicians. For example, using AI-based semi-automated imaging, a clinician can make improved decisions regarding diagnosis and treatment of stroke in patients since the clinician can view the patient's brain from different angles/views that highlight or visually represent volumes of interest indicative of stroke.

As another example, the disclosed technology provides for fast and precise detection and quantification of brain volumes, regardless of size and morphology. This can be advantageous to more accurately and quickly identify acute stroke in patients or other subjects. More accurate and fast identification of stroke can also result in more informed decisions to be made, automatically by a computer system or manually by a clinician, with regards to treatment.

As yet another example, the disclosed technology provides for precise identification of small sub-milliliter infarct volumes. These volumes can be critical in identifying stroke etiology. Identifying the tiny infarct volumes can be accomplished by automatic, AI-based measurement of absolute (in ml) and relative (in terms of % of total brain volume) infarct burdens on initial brain image data. By automatically identifying and quantifying such small infarct volumes, the disclosed technology can provide a clinician with more ability to accurately diagnose and treat stroke events.

The details of one or more implementations are set forth in the accompanying drawings and the description below. Other features and advantages will be apparent from the description and drawings, and from the claims.

BRIEF DESCRIPTION OF THE FIGURES

The patent or application file contains at least one drawing executed in color. Copies of this patent or patent application publication with color drawing(s) will be provided by the Office upon request and payment of the necessary fee.

Like reference symbols in the various drawings indicate like elements.

DETAILED DESCRIPTION

This document generally relates to identifying strokes from brain image data using AI-based techniques and processes, such as machine learning algorithms and models. The disclosed technology can be used to aid clinicians, medical professionals, and other users in 1) identification of stroke mechanisms and/or etiology based on 3D-morphology of brain image data, 2) measuring quantitative presentation and interval changes of ischemic and/or hemorrhagic strokes, 3) establishing a quantitative foundation for a systematic approach to guide diagnostic and therapeutic approaches, and 4) functioning as a biomarker for cerebrovascular disease.

The disclosed techniques employ AI-enhanced imaging for diagnosis and therapy of acute stroke in patients and other subjects (e.g., mammals, including humans and animals). The disclosed techniques provide for employing semi-automated and/or automated high-performance computing for multidimensional (e.g., 3D volumes, multiple modalities, time, etc.) image processing. Therefore, the disclosed techniques can allow for more accurate and quicker detection and quantitative volumetric analysis of ischemic and hemorrhagic strokes in brain image data (e.g., CT head image data, MRI brain imaging). Using this analysis, users, such as clinicians, can make more accurate determinations about stroke diagnosis, treatment, and therapeutics.

Figure 1A:
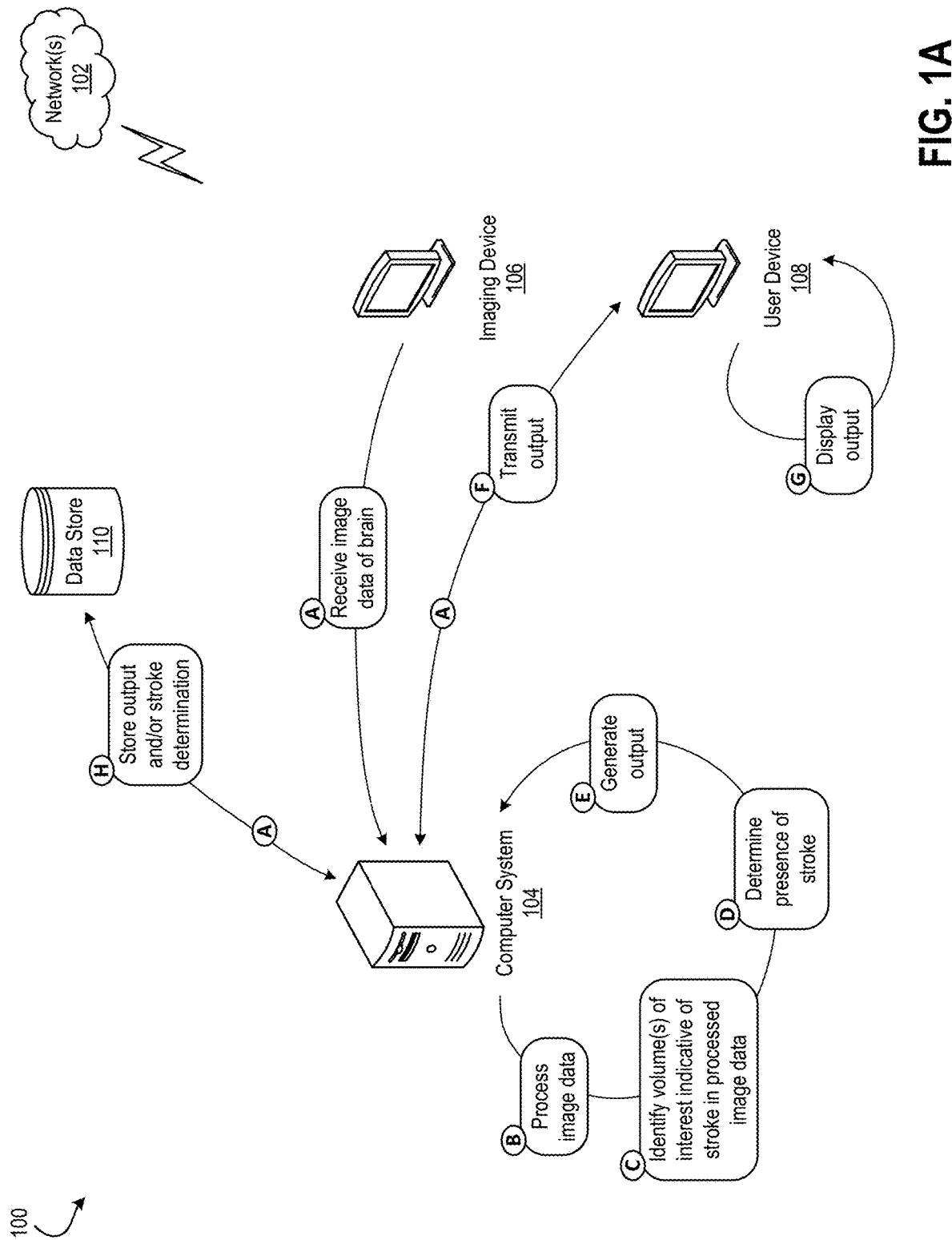
FIG. 1A is a conceptual diagram of an example system for identifying stroke in a patient using AI-based techniques.

Referring to the figures, FIG. 1A is a conceptual diagram of an example system 100 for identifying stroke in a patient using AI-based techniques. The system 100 includes a computer system 104, imaging device 106, user device 108, and data store 110, which can communicate (e.g., wired and/or wireless) via network(s) 102. In some implementations, one or more of the computer system 104, imaging device 106, user device 108, and data store 110 can be part of a same computer, system, and/or network of devices and/or computers. For example, the imaging device 106 and the user device 108 can be a same device. Moreover, the computer system 104 can be remote from the other components of the system 100. The computer system 104 can also be part of a network of devices and/or systems, such as being part of a medical facility's infrastructure. The computer system 104 can also be a cloud-based service.

Referring to FIG. 1A, image data of a subject's (e.g., patient) brain can be received at the computer system 104 (step A). The image data can be received from the imaging device 106, the user device 108, and/or the data store 110. In some implementations, the image data can be transmitted from the imaging device 106 once the image data is captured by the imaging device 106. In some implementations, the image data can be transmitted from the user device 108 when a clinician or other relevant user reviews the image data after it has been captured by the imaging device 106. The user can, for example, select an option at a GUI presented at the user device 108 to process the image data. Selecting this option can cause the image data to be transmitted to the computer system 104 in step A. In some implementations, the image data can be retrieved from the data store 110 when the computer system 104 performs processing on the image data or a batch of image data at a time that is later than when the image data was initially captured. As described throughout this disclosure, the image data can be DICOM data. The image data can also be one or more other types of brain imaging data, such as CT scans, MRIs, and x-rays.

The computer system 104 can process the image data (step B). Processing can include performing one or more analyses to refine the image data. As a result of processing, the computer system 104 can more accurately make determinations about whether the image data indicates a stroke event for the particular patient. As described further below, processing can include applying filtering, segmenting, and/or morphological neighborhood operations to the image data. Processing the image data can also include extracting personally identifying information from the image data (e.g., header data) to preserve patient privacy.

In some implementations, one or more machine learning models can be trained and used by the computer system 104 to process the image data.

Once the image data is processed, the computer system 104 can identify volumes of interest indicative of stroke in the image data (step C). The computer system can employ techniques such as a flood fill algorithm to identify volumes of interest. For example, the computer system can use the flood fill algorithm to detect 3D connected volumes within a certain pixel threshold in the image data. The 3D connected volumes must meet certain pixel upper and lower limits typically indicative of stroke in order to be connected. In some implementations, such volumes may be connected if they have 26 connectivity. The computer system may continue to determine whether 3D volumes of interest meet a same criteria or definition to be linked until the computer system runs into a barrier. The barrier can be a situation where two volumes of interest do not satisfy a same definition, criteria, or rule. For example, the computer system can determine whether each voxel has a density of a same value and/or a density within some threshold range. As an illustrative example, in an array of cells, where each cell represents a voxel, any cells that are near each other and have densities of 1 (or another predetermined value) can be identified as meeting the same criteria and thus connected. Any cells that are near each other and do not have densities of 1 (or another predetermined value) may not be connected.

Accordingly, like pixels can be clustered together. The cluster of like pixels can then be measured to determine a total volume. The computer system may also adjust sensitivity to identify different volumes of interest. Therefore, in some implementations, the computer system can identify and connect volumes of interest that have a smallest predetermined pixel size. The computer system can also identify and connect volumes of interest having any other predetermined pixel size. Moreover, in some implementations, the computer system can utilize one or more machine learning models to suggest settings, such as pixel size, criteria, definitions, or other rules that can be used to connect 3D volumes of interest.

The computer system can also be trained to scan the entire brain in the image data to identify all volumes of interest, sort the volumes of interest by size (e.g., volume size), and then determine whether each of the sorted volumes (e.g., from largest volume to smallest volume) is indicative of a stroke.

Using the techniques described herein, the computer system 104 is able to identify single voxel volumes, which means stroke determinations can be made using a on a single voxel basis, which is the highest resolution highest resolution of an CT or MRI. This can be advantageous to detect all possible volumes of interest in the brain on a more granular level, which can otherwise be challenging or impossible.

Figure 7:
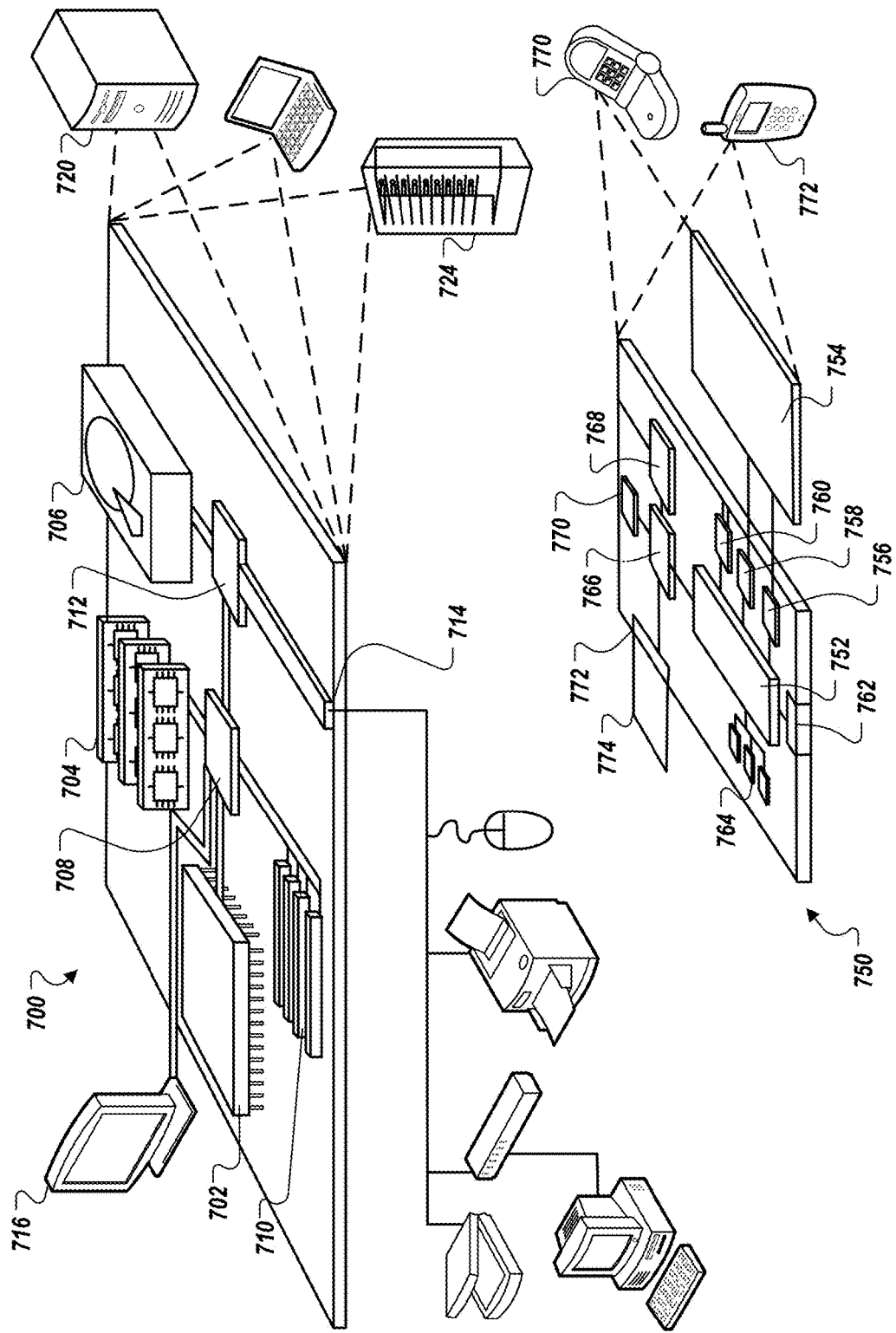
FIG. 7 shows a diagram of an exemplary computer processing system that can execute the techniques described herein.

In some implementations, the computer system 104 can utilize one or more machine learning models to identify the volumes of interest in multidimensional space. For example, the computer system 104 can identify volumes of interest that are connected in 3D space. The models can, for example, be trained to identify portions of training image data of brains that contain infarcts indicative of stroke events. The models can be trained to identify volumes of interest that are unique to different types of strokes. Such models can be continuously improved based on identifications made by the computer system 104 during runtime. Therefore, the models can be improved to more accurately detect stroke events. The models can also be improved to accurately detect stroke events by identifying even smaller volumes of interest. Refer to FIG. 7 for further discussion about training the models.

The computer system 104 can determine a presence of stroke (step D). Once the volumes of interest are identified, the computer system 104 can analyze such volumes and determine whether they in fact represent a stroke event for the particular patient. The computer system 104 can, for example, assign confidence scores to each of the identified volumes of interest, where the confidence scores indicate likelihood that the volume of interest is indicative of a stroke event. If any of the assigned confidence scores exceed a threshold level, the computer system 104 can determine that a stroke event in fact exists for the particular patient. The computer system 104 may also quantify a severity of the stroke event. The stroke event may be quantified based on the assigned confidence score(s), a size of one or more volumes of interest, and/or a presence of multiple volumes of interest.

The computer system 104 can generate output (step E). The output can include visual representations of the patient's brain image data with the identified volumes of interest overlaid and represented in an indicia different than the indicia of the patient's brain. Refer to FIGS. 3-6 for further discussion. The output can also include textual or numeric information about the identified volumes of interest and the presence of stroke. The output can include confidence scores that the patient has a stroke event, predictions about effects that the stroke event would have on the patient, predicted severity of the stroke event for the patient, and/or suggestions for diagnosis and/or treatment for the patient. One or more other outputs can also be generated by the computer system 104.

The computer system 104 can transmit the output to the user device 108 (step F). The user device 108 can display the output (step G). The user at the user device 108 can interact with the output, such as selecting different views of the brain image data to view the identified volumes of interest relative to other portions of the brain. The user can also use the output to make informed and accurate decisions about the patient's condition, diagnosis, and treatment. As a result, the computer-generated output can provide a semi-automatic solution to the user that improves their efficiency and accuracy in analyzing a patient's brain, identifying stroke events, diagnosing the patient, and making other medical or clinical decisions.

The computer system 104 can store the generated output and/or stroke determination in the data store 110 (step H). The output and/or stroke determination can be retrieved and used in future analysis by the computer system 104 or another computing system (e.g., a cloud-based computing system that is used by a hospital infrastructure). As an example, the visual representations of the identified volumes of interest overlaying the image data can be used in future population analysis and research studies.

In some implementations, steps A-H can be performed on image data of one patient's brain. Processing and analyzing the one patient's brain can be performed in real-time, for example, at or around a same time that the patient's brain is being imaged by the imaging device 106. The processing and analyzing can also be performed some time after the patient's brain is imaged. In some implementations, steps A-H can be performed on a batch of image data representing multiple different patients' brains. Thus, image processing and analysis can be performed at once, which can more efficiently utilize available computing resources.

Figure 1B:
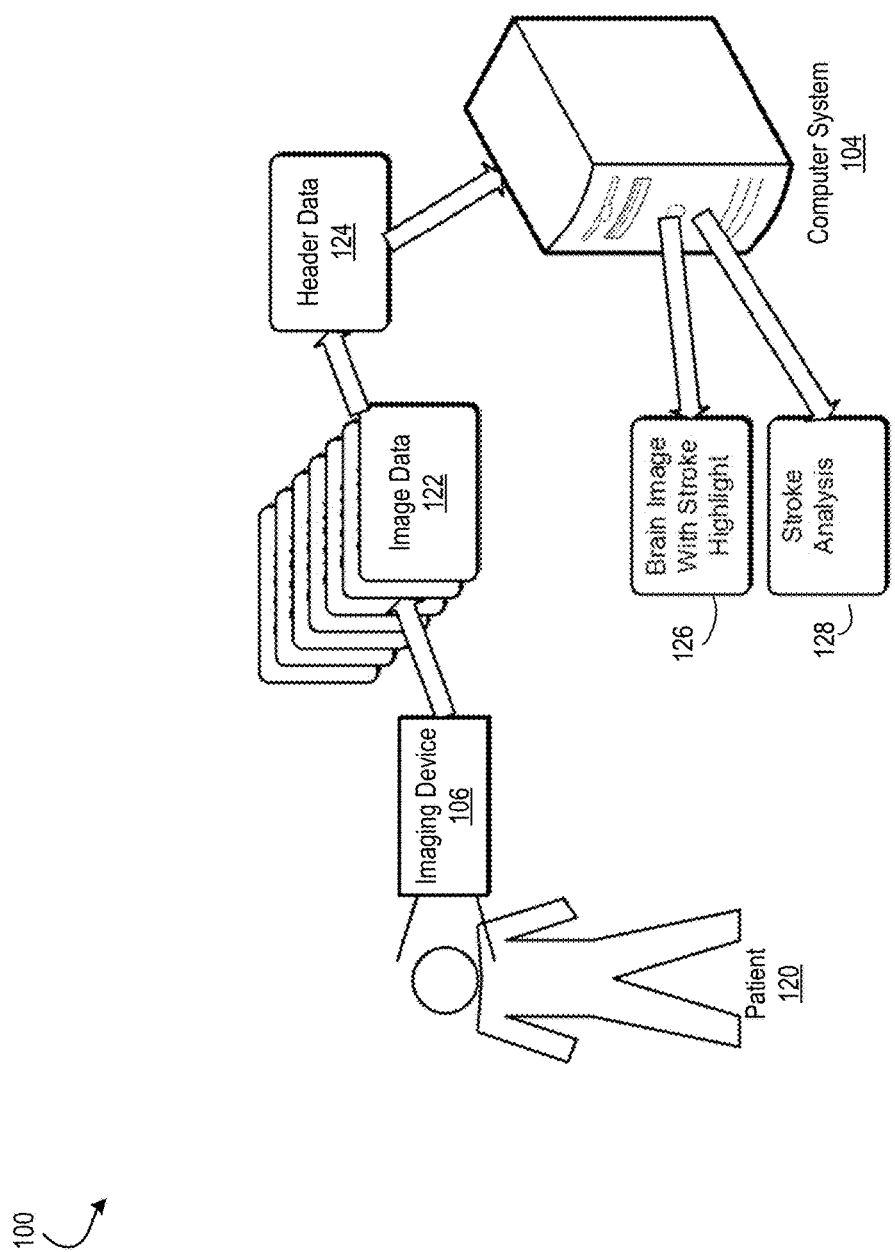
FIG. 1B illustrates a schematic of an example system for performing the techniques described herein.

FIG. 1B illustrates a schematic of the example system 100 for performing the techniques described herein. The system 100 can be used for automated identification of volumes of interest in volumetric brain images or other brain image data. A patient 120 can be imaged by the imaging device 106 in order to gather data that can be used to identify, by the computer system 104, stroke infarct volume in the patient 120's brain. For example, the patient 120 can be subjected to an x-ray, a CT scan, an MRI scan, or any other type of imaging performed by the imaging device 106. The patient 120 can be a mammal, such as a human or an animal.

Imaging the patient 120 can produce one or more image data 122. In some implementations, imaging the patient 120 can result in generation of DICOM images. Other types of images may also be generated, such as brain image data that is derived from CT scans, MRIs, and x-rays. The DICOM images, for example, capture many two dimensional (2D) slices of the patient 120's brain that can be stacked to create 3D volumetric images. In some cases, the 2D slices can also be used to generate 4D volumetric images in a time domain. Such volumetric images can be utilized by the computer system 104 to more accurately determine different volumes of interest (e.g., infarcts) in the patient 120's brain.

In addition, the DICOM images (or other brain image data 122) may include header data 124, such as a manufacturer of the imaging device 106, a timestamp of the imaging, etc. The header data 124 may or may not provide information about the patient 120's condition or brain. In some implementations, the header data 124 may include private information about the patient 120 or other personally identifying information, such as the patient 120's age, weight, name, birthdate, and/or unique identifier.

As described herein, the computer system 104 can receive the image data 122 (e.g., the DICOM images) and extract the header data 124. Extraction can be performed using known techniques, software, and/or applications. One or more machine learning algorithms and/or models can also be used by the computer system 104 to automatically identify header data 124 (or particular portions of the header data 124 that should be removed, such as personally identifying information) and extract the header data 124. In some cases, portions of the header data 124 may be discarded (e.g., redundant data, private information not needed for the disclosed techniques and processes, other personally identifying information, etc.). Supplementary information may be generated in part by using the extracted header data 124. The supplementary information can include data about the patient 120 that can populate health records associated with the patient 120. Supplementary information can also include data about the imaging that was performed, such as a time and data, which can be useful if a clinician seeks to compare image data analysis from one time period to another time period. The header data 124 may also be aggregated, compressed, and/or used to look up other data about the patient 120, the imaging device 106, and/or the patient 120's condition. In some implementations, the header data 124 can be used to glean more information about the patient 120 and to more accurately diagnose and treat the patient 120's condition.

The computer system 104 may also access additional image information in the image data 122. As an example, the computer system 104 can access the image data of the DICOM images. This image data may include pixel or voxel values that store information reflecting phenomenon of the patient 120 at the time of imaging. For example, in some cases, imaging performed by the imaging device 106 may generate one or more pixel values that correspond to fat tissue, one or more other pixel values that corresponds to contrast dye, one or more other pixel values that corresponds to bone, etc. This information can be used by the computer system 104 to more accurately identify volumes of interest in the patient 120's brain (e.g., by analyzing and correlating pixel values or voxel values), to determine a condition of the patient 120's brain, and to provide for more accurate diagnosis and treatment determinations.

The computer system 104 may generate, from the header data 124 and the image data 122, one or more useful outputs. The outputs can be used by a clinician to more accurately and quickly analyze the patient 120's brain and make diagnosis and treatment decisions. One such output can be a graphical representation 126 of the patient 120's brain with possible stroke areas (e.g., volumes of interest) highlighted or identified in some other indicia. For example, the computer system 104 may reserve one or more colors (e.g., bright orange or red) for portions of the brain that the computer system 104 identifies, using machine learning models, as likely indicative of stroke events or volumes of interest. The computer system 104 can be configured to tint one or more pixels of the identified portions of the brain in the graphical representation 126 such that when the graphical representation 126 is viewed by the clinician, the clinician's attention is drawn/directed to the tinted portions. The clinician, therefore, is directed to review the particular tinted portions in the graphical representation 126. Such visual indicators can be advantageous to reduce an amount of time needed by the clinician to analyze the patient 120's entire brain and locate volumes of interest therein. Moreover, the visual indicators make it easier to identify fine details or shapes indicative of possible stroke events that may be difficult to quickly spot or identify at all with the human eye. Rather, the clinician can direct their attention and expertise to the tinted portions in the graphical representation 126 of the brain, and spend their time appropriately diagnosing and treating the patient 120's condition.

Another example output is a stroke analysis 128 that can include textual and/or numerical information about the patient 120's brain. The stroke analysis 128 and the graphical representation 126 of the brain can both be outputted at a user device of the clinician (e.g., the user device 108 in FIG. 1A). In some implementations, the stroke analysis 128 or the graphical representation 126 can be outputted. In some implementations, the clinician can select a preferred form of output, which can then be outputted and presented at the user device of the clinician.

The textual and/or numerical information of the stroke analysis 128 can be determined by the computer system 104 using AI techniques, as described herein. For example, a stroke-risk score may be calculated for the patient 120, using one or more machine learning models. The stroke-risk score can represent a computed likelihood that volumes of interest identified in the image data 122 are indicative of stroke for the patient 120. The stroke-risk score may be a value on a scale of 0 to 1. One or more other scales or ranges of values can also be used (e.g., 0 to 100, Boolean or string values such as "true" and "false," etc.).

As described herein, the computer system 104 can be trained, using AI techniques such as machine learning trained models, to identify portions in the image data 122 that may be indicative of stroke (e.g., infarcts, volumes of interest) and assign a confidence value as to how likely the identified portions are associated with stroke (e.g., the stroke-risk score). The confidence value can be compared, by the computer system 104, to a threshold value. If the confidence value is greater than the threshold value, the computer system 104 can classify the patient 120's brain as likely having indications of stroke. In such a case, the graphical representation 126 can also be augmented to provide a visual indication to the clinician about the possible stroke. The visual indication can include but is not limited to a warning graphic, an audible alarm, etc. One or more other outputs can also be generated by the computer system 104 using the techniques described throughout this disclosure.

Figure 2:
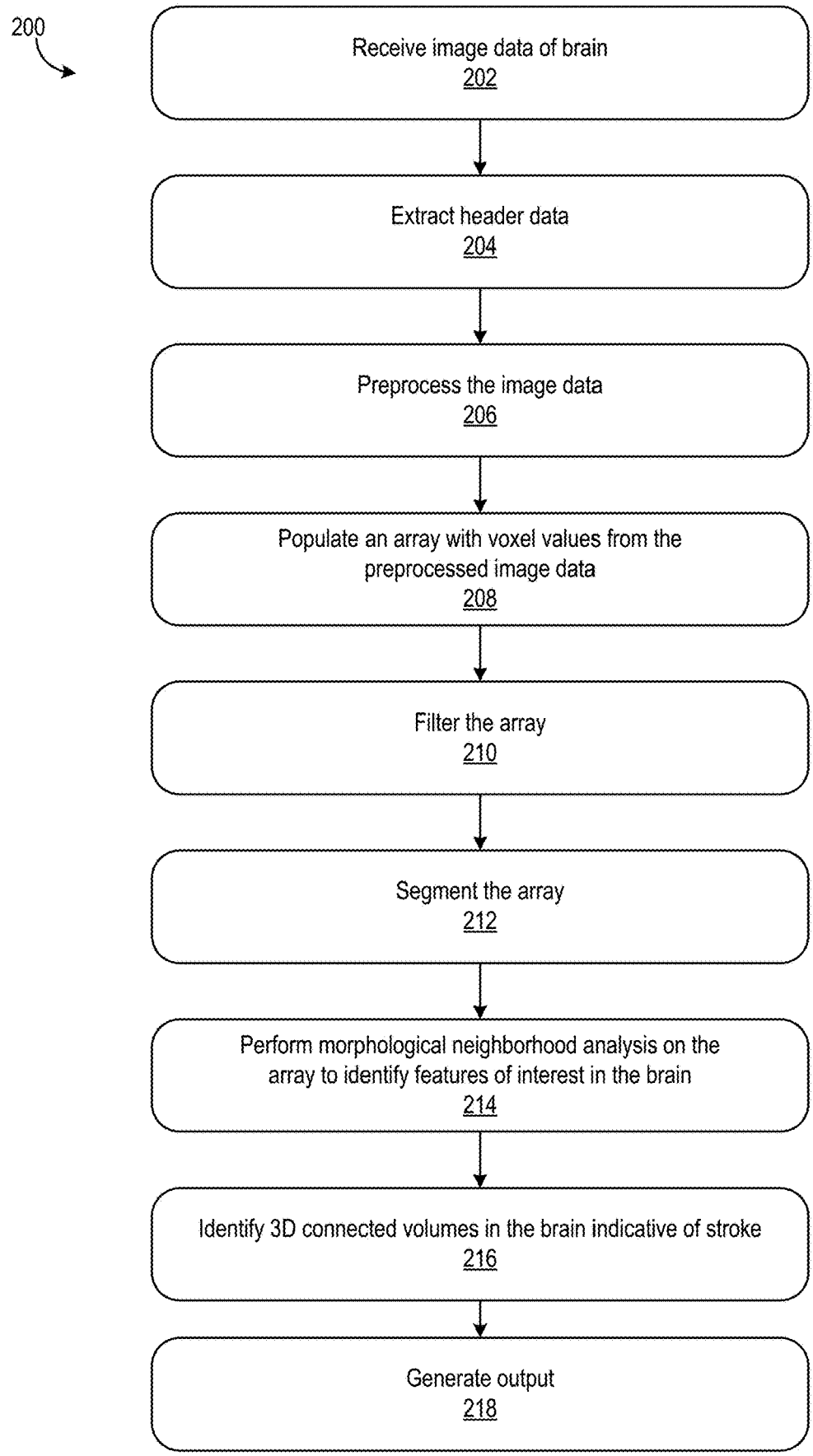
FIG. 2 is a flowchart of a process for automatically identifying volumes of interest in brain image data that may be indicative of stroke.

FIG. 2 is a flowchart of a process 200 for automatically identifying volumes of interest in brain image data that may be indicative of stroke. The process 200 can be performed by the computer system 104. The process 200 can also be performed by one or more other computers, systems, servers, network of servers, devices, and/or cloud-based services. For illustrative purposes, the process 200 is described from a perspective of a computer system.

Referring to the process 200, image data of a brain is received in 202. A DICOM image and/or multiple DICOM images can be received from an imaging device (e.g., the imaging device 106 depicted in FIG. 1A), as described above. One or more other types of images can be received. The computer system 104 can be physically remote and communicably coupled to the imaging device 106 and may receive, over a secure computer network, a DICOM image created by the imaging device 106. The image can be generated using one or more technologies such as CT, MRI, and/or other technologies.

The image can include a variety of additional information. For example, the image can include time series data. A patient of the imaging can be administered a contrast dye. Imaging may be recorded as the dye washes into the subject's brain such that the dye is saturated in the brain. Imaging may also be recorded as the dye washes out of the brain. The contrast dye can make portions of the brain more apparent and differentiated from other portions of the brain in the image. The image can include other information, such as header data. The header data can indicate information about the imaging device, when the image was captured, what settings were used to capture the image, as well as information about the patient whose brain is imaged. The header data, for example, can include personally identifying information, such as the patient's name, age, date of birth, and/or patient identifier.

Accordingly, header data is extracted in 204. Data in the header relevant to processes described throughout this disclosure can be copied, stored in another data file or object, and/or used in other processes and analyses. Other data in the header, such as personally identifying information, may be ignored, discarded, or otherwise removed from the image data. For example, header data may be extracted to comply with personal health information requirements, such as HIPPA or other security requirements, such as FERPA or FISMA. Sometimes, header data may be extracted if it obstructs imaging views of the brain, thereby making subsequent image processing more accurate.

The image data can be preprocessed in 206. For example, image data of the DICOM image or DICOM images can be preprocessed. The image data can include voxel or pixel values in addition to the header data. For example, the volumes can be determined by an MRI scanner and can be included in DICOM data (e.g., header data). Each of the voxel values can represent different objects or portions in the patient's brain. When the voxel values are counted, grouped, and analyzed by the computer system (e.g., using machine learning models and other AI techniques described throughout this disclosure), the voxel values can reveal information about a condition of the patient's brain. For example, some voxel values can be grouped by the computer system into volumes of interest that represent infarcts. Grouping the voxel values can be beneficial to calculate stroke volumes and estimate actual brain volume. The calculated stroke volumes and actual brain volume can be used by the computer system to measure a stroke in ml measurement and/or percent of brain volume. The computer system can then analyze these grouped values to determine whether the patient has a stroke event, risk of having a stroke, and/or a relative burden of the infarcts on the brain. As another example, some voxel values can be grouped into volumes of interest that represent an interruption in blood supply of the brain at a time of imaging. The computer system can glean further insight into the condition of the patient's brain based on identifying this interruption in blood supply.

An array can be populated with voxel values from the preprocessed image data in 208. For example, for a 4D image, a 4D array of a same size may be created and values determined for the voxels may be placed into the corresponding cells of the 4D array. The array can be generated in one or more other dimensions, including but not limited to 2D, 3D, 5D, etc.

The computer system can perform a filtering analysis on the array to generate a filtered array (210). Filtering can include identifying a subset of cells in the array to exclude from the array and removing the identified subset of the cells to generate the filtered array. For example, some but not all of the cells of the array may be tagged as filtered out of future analysis. In some implementations, the computer system can be trained, using AI or machine learning techniques, to identify features of interest and/or identify features that are not of interest in the array. For example, machine learning models can be trained using training data sets to identify features of interest. Anything that has not been identified as features of interest can be discarded from the array. Machine learning models can also be trained to identify features that are not of interest, to select such features in the array, and to update the array by removing such features from the array. Machine learning and other AI-based techniques can also be used to improve the computer system's accuracy in identifying features of interest and/or features that are not of interest and removing the features that are not of interest from the array. The features not of interest may include cells representing locations outside of the subject's head (e.g., the subject's neck or shoulders). Since features that are not of interest are removed from the array, the computer system can more efficiently utilize computing resources by only analyzing cells in the array that correspond to features of interest. In some implementations, filtering can be optionally performed.

The computer system can also perform a segmenting analysis to generate a segmented array (212). The segmenting analysis can be performed on the filtered array from block 210. Sometimes, the filtering analysis may not be performed, and the computer system may only perform the segmenting analysis. In some implementations, the computer system may perform the segmenting analysis before the filtering analysis. Applying the segmenting analysis can include segmenting the cells of the filtered array based on physiological structures of the brain. Like the filtering analysis, machine learning or other AI-based techniques and/or models can be used by the computer system in some implementations to accurately identify and group cells in the array based on known structures in the brain. One or more machine learning models can, for example, be trained, using training data sets, to identify different types of physiological structures of the brain based on annotated and labelled voxel values. Output from the models can be groupings of cells in the array, where each grouping corresponds to a different physiological structure of the brain.

Using the techniques described herein, the computer system can, for example, segment the cells of the filtered array into various volumetric geometries that represent structures of the patient's brain and surrounding tissue in the brain. This can include blood vessels, brain tissue, bone, etc. This segmenting analysis may be limited only to the cells that have not been filtered out in the previous filtering process. As mentioned above, in some implementations, the segmenting analysis can be performed on all cells in the array, and the analysis can be targeted at identifying particular physiological structures of interest in the brain. Moreover, performing segmenting analysis can be beneficial to ensure that the computer system accurately analyzes areas of interest in the brain for indications of stroke.

The computer system can perform morphological neighborhood analysis on the array to identify features of interest in the brain (214). As a result of this analysis, the computer system can generate a features relationship array. The features relationship array can include features of interest in the brain that are indicative of stroke. Performing morphological neighborhood analysis can include identifying features of interest in the segmented array based on connectivity data amongst the cells in the segmented array. In some implementations, the morphological neighborhood analysis can be performed on the filtered array from block 210. In yet some implementations, the morphological neighborhood analysis can be performed on the array from block 208.

As described above with regards to the filtering and segmenting analyses, in some implementations, the computer system can utilize one or more machine learning models that are trained, using brain image training data sets, to identify connectivity data and make associations between connectivity data of the cells in the array (e.g., remaining cells in the segmented array). The models can be trained to identify connectivity data that exists within some predetermined threshold range. If the connectivity data exists within the predetermined threshold range, the computer system can determine that the connectivity data is associated with a particular feature of interest. That feature of interest can be an infarct that is commonly associated with stroke events. As a result of morphological neighborhood analysis, the computer system can group cells of the array that indicate features of interest. Grouping the cells can be advantageous to generate/visualize 3D volumes of the features of interest, which can further be used by the computer system and/or a clinician to analyze and diagnose the patient's condition.

Accordingly, the computer system can identify 3D connected volumes in the brain that are indicative of stroke in 216. In some implementations, the computer system can identify connected areas of interest in the brain in any other dimension, including but not limited to 2D, 4D, 5D, etc. Using techniques such as a flood fill algorithm, machine learning models, and/or other AI-based techniques, the computer system can determine information about the 3D connected volumes. For example, in some implementations, one or more of the models can be trained with template shapes that represent possible stroke volumes in a brain. The models can be trained to match identified volumes of interest in the brain image data to the template shapes. If there is a match, the computer system can determine that the matching volume of interest is indicative of a stroke. The template shapes can also correspond to different types of strokes or different symptoms, diagnoses, treatments, and/or side effects. Thus, when a volume of interest is identified to be matching a template shape, the computer system can generate output that includes information associated with the matching template shape (e.g., type of stroke, potential symptoms, potential diagnosis, potential treatments, potential side effects, etc.).

As another example, in 216, the computer system can determine a volume of each identified feature of interest, a relative burden of the volume on a total volume of the brain, what type of infarct or other physiological structure is represented by the 3D connected volume(s) (e.g., watershed infarcts, embolic infarcts, etc.), etc. The computer system can also classify and identify what type of stroke the patient may experience, such as ischemic or hemorrhagic stroke.

In some implementations, identifying the 3D connected volumes of interest can include determining a volume of the feature of interest represented by the 3D connected volumes of interest. For example, the computer system can determine in infarct volume. Determining the volume can be based on counting voxel values within a predefined region of the image data, where that predefined region corresponds to the feature of interest (e.g., an infarct). The computer system can also determine a total volume of the brain based on counting voxel values within a region of the image data that corresponds to the patient's brain. Thus, voxel values in space surrounding the brain may not be counted. Moreover, the computer system can determine relative infarct burden in percent of brain volume for each of the 3D volumes of interest. The relative infarct burden can be a ratio between each of the 3D volumes of interest and the computed total volume of the brain.

As yet another example, in 216, the computer system can determine a type of stroke from the 3D connected volumes of interest in the brain. The stroke can be an ischemic stroke, a hemorrhagic stroke, or a transient ischemic attack. One or more machine learning models can be trained to classify identified volumes of interest with identified types of strokes. Output of the models can be an indication of the type of stroke represented by the 3D connected volumes of interest in the brain image data.

Moreover, identifying the 3D connected volumes of interest can include determining a confidence interval or value that indicates likelihood that a particular volume of interest (e.g., shape in the array) represents a stroke event or infarct. The confidence interval can also indicate likelihood that a collection of volumes of interest represents a stroke event or infarct. The higher the confidence interval (e.g., the confidence interval exceeds some predetermined threshold value), the more likely identification of the stroke event or infarct is accurate. The lower the confidence interval (e.g., the confidence interval is less than some predetermined threshold value), the less accurate the one or more models are in identifying stroke events or infarcts (e.g., the computer system is less certain that it made an accurate identification using the models). The confidence interval can then be used, by the computer system or another computing system, to continuously train and improve accuracy of the models.

The 3D volumes of interest can be measured in unit measurements. For example, the measurement units can be milliliters or cubic centimeters. As a result, the computer system can make more granular identifications of volumes of interest, thereby resulting in more accurate determinations of stroke events in any brain. The computer system can detect smaller features in the brain indicative of stroke that the human eye may otherwise not be able to readily identify or analyze.

In 218, the computer system can generate output. As part of block 218, results of the process 200 may be recorded in computer memory, displayed in a GUI presented at a user device (e.g., the user device 108), transmitted to another system for further processing, analysis, and/or storage, and/or otherwise used by a computer or other device. The results of the process 200 can be stored in a data store (e.g., the data store 110). The results can then be retrieved from the data store at another time for further analysis and processing. Moreover, the computer system can generate output for display at the user device (e.g., clinician's mobile device, smartphone, laptop, tablet, computer, etc.) that indicates the identified 3D volumes of interest. The output can include visual representations of the features in the brain that are indicative of a stroke event and/or infarct volumes. The visual representations can include the brain image data overlaid with the identified 3D volumes of interest, where the identified 3D volumes of interest can be tinted, colored, or highlighted in a color that is different than the original colors of the brain image data. Refer to FIGS. 3-6 for further discussion on visual output. One or more other indicia can also be used.

For example, the computer system can superimpose the identified 3D volumes of interest on predefined regions of the image data. In other words, features of interest that were identified in block 214 can be mapped onto (e.g., overlaid on) the image data that was received in 202. The image data can therefore be updated to visually depict the features of interest, which can be indicators of stroke (e.g., infarcts). As described throughout this disclosure, the features of interest can be tinted one or more different colors to bring a user's attention to those areas in the image data. For example, features of interest having volumes that are within a first range (e.g., highest volume) can be tinted a first color, such as red. Features of interest having volumes that are within a second range (e.g., medium-sized volume) can be tinted a second color, such as green. Features of interest having volumes that are within a third range (e.g., smallest volume) can be tinted a third color, such as purple. The different colors can be beneficial to direct the user's attention and analysis to the features of interest having the highest volumes, which may have a larger impact on the condition of the patient's brain, in comparison to features of interest having the smallest volumes in the patient's brain. Regardless, color-coding the features of interest can also be beneficial to direct the user's attention to the features of interest so that the user does not have to spend their time analyzing all portions of the patient's brain in the image data If no features of interest are identified in block 214, for example, then no features of interest may be superimposed on the brain image data in block 218. In other words, white and grey matter in the brain image data may not be altered or modified. No features in the brain may be tinted or otherwise shaded a color that is reserved for the varying volumes of interest described above As another example, the computer system can generate as output, for display at the user device, coronal and sagittal views of the 3D volumes of interest in the brain image data. The coronal and sagittal views can be used, automatically by the computer system or manually by the clinician or other user, to determine stroke etiology. The coronal and sagittal views can also be used by the clinician or other relevant stakeholder to make determinations about the patient's diagnosis, treatment, and/or stroke etiology. Such additional views can make it easier for the clinician to view and analyze the patient's brain from different perspectives. The clinician can therefore have a more wholesome view and understanding of the patient's brain, which benefits the clinician in more accurately diagnosing and treating the patient's condition.

In some implementations, the process 200 can be performed multiple times for the same patient in order to identify how a stroke event or infarcts change over time for that particular patient. For example, volumetric images of the patient's brain can be taken at a series of time points (e.g., time course) in which the stroke event or infarct volume can be measured within each time point to identify how the stroke event or infarct volume changes over one or more different periods of time.

In some implementations, the process 200 can also include volume-based stroke scoring. The larger the stroke event or infarct, the larger the volume-based stroke score. The score can be an extent of damage to the patient's brain and overall health or medical condition. The score can be measured in terms of ml measurements or percent of total brain volume. Thus, a volume of interest (e.g., stroke) that has a score value of 2% of total brain volume can indicate that 2% of the patient's total brain volume is lost from the identified stroke event. In some implementations, the score may be likelihood of stroke for the particular patient.

In some implementations, the process 200 can also include generating an outcome prediction. The outcome prediction may include predictions of the patient's physical or cognitive abilities after the stroke event that has been identified using the process 200. The computer system can use one or more machine learning models that have been trained using labelled/annotated training data to correlate severity of stroke events with consequences on the patient's health. Using such models, the computer system can more accurately predict side effects that the patient may experience based on their stroke event(s).

In yet some implementations, the computer system can make predictions regarding effectiveness of various therapies for the particular stroke event that the patient experienced. The computer system can use one or more machine learning models, AI techniques, and patient data about the patient to predict their response to different therapies. Sometimes, the computer system can also make suggestions about what therapies should be prescribed to the patient based on the predicted responses to different types of therapies.

Figure 3:
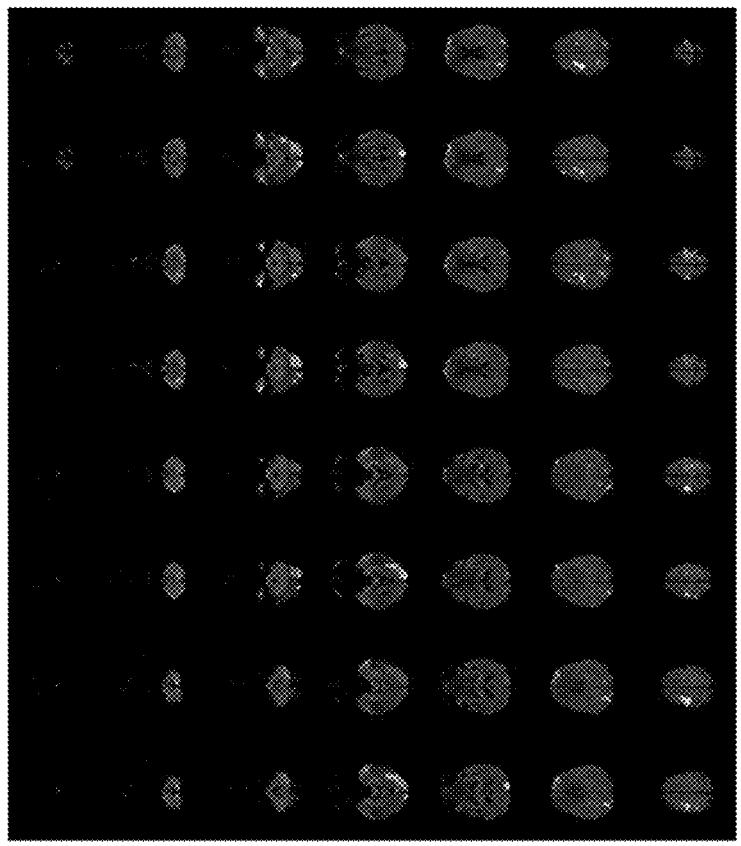
FIG. 3 depicts example results of AI-based volumetry of watershed and embolic infarcts in a patient's brain.
Figure 3:
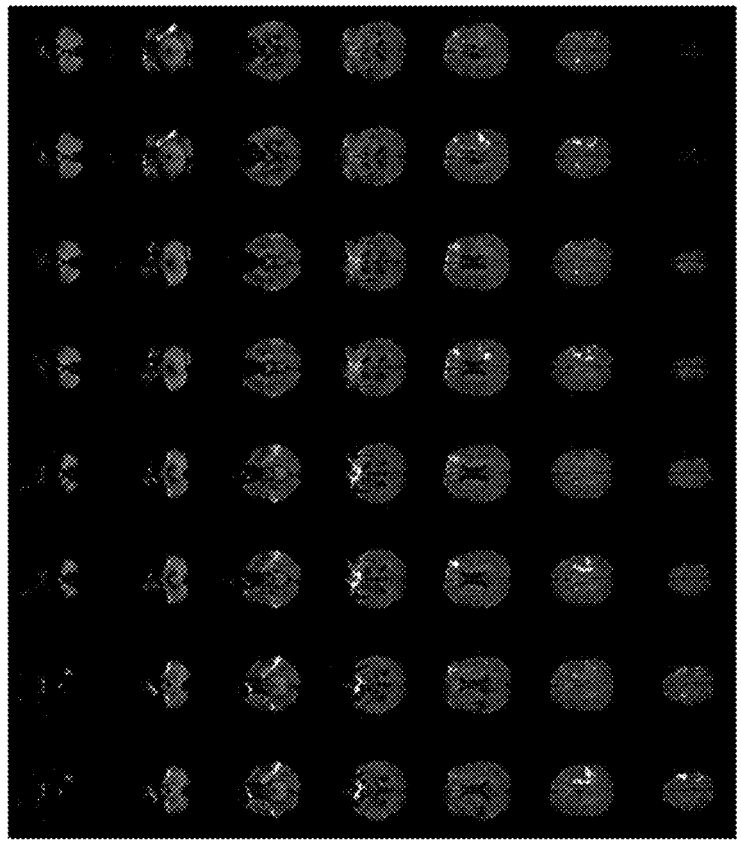

FIG. 3 depicts example results of AI-based volumetry of watershed and embolic infarcts in a patient's brain. Identified infarcts can be ordered by volume and pseudo-colored in one or more color sequences. Here, a 6-color sequence is used: red-orange-yellow-green-blue-purple. Red represents a largest identified volume of the infarct(s) and/or a volume that is greater than a first predetermined threshold level. Purple represents a smallest identified volume of the infarct(s) and/or a volume that is less than another predetermined threshold level. In some implementations, if more than 6 volumes are identified, the color sequence can start over with red, and can repeat until all volumes have been identified and pseudo-colored. One or more other color sequences and/or indicia (e.g., patterns, straight lines, dotted lines, other textures, etc.) can be used to visually depict the different infarct volumes in the brain.

Image data 300 depicts AI-based volumetry of watershed infarcts using the techniques described throughout this disclosure (e.g., refer to FIGS. 1-2). 5 ischemic sub-volumes have been identified by the computer system 104. For example, the computer system 104 can apply a machine learning model to the brain image data that is trained to identify watershed infarcts. The computer system 104 has also identified an overall infarct volume of 23.6 ml and a relative infarct volume of 2% of the total brain volume of 1,152 ml. These values indicate that because of the identified stroke, the patient has lost 2% of their total metabolically-active brain volume. The computer system 104 can apply one or more machine learning models to the brain image data to compute volumes of the identified watershed infarcts and the total volume of the brain. Moreover, the computer system 104 can apply one or more machine learning models to tint/colorize portions of the brain image data that represent the identified watershed infarcts. The portions of the brain image data can be tinted based on the identified volume of each of the watershed infarcts. Thus, red portions of the brain image data can represent the largest volume watershed infarcts that were identified by the computer system 104 and one or more other colors can be used to represent different volume sizes of the identified infarcts.

Image data 302 depicts AI-based volumetry of embolic infarcts using the techniques described throughout this disclosure. Here 20 ischemic sub-volumes have been identified by the computer system 104 with an overall infarct volume of 51.6 ml and a relative infarct volume of 4.4% of the total brain volume of 1,178 ml. Here, the patient has lost 4.4% of their total brain volume due to the identified stroke. Such determinations are made by the computer system 104 when one or more machine learning trained models are applied to the raw brain image data, as described throughout this disclosure.

The image data 300 demonstrates fewer volumes of watershed infarcts overlaid on the brain image data. The identified volumes of interest are pseudo-colored red and orange, with very small/discrete portions or volumes of interest pseudo-colored green. The image data 302 demonstrates significantly more volumes of embolic infarcts overlaid on the brain image data. The identified volumes of interest are pseudo-colored using the 6-color sequence. Thus, the overall infarct volume of 51.6 ml is comprised of varying volumes of infarcts throughout the brain, as depicted in red, orange, yellow, green, blue, and purple indicia.

Figure 4:
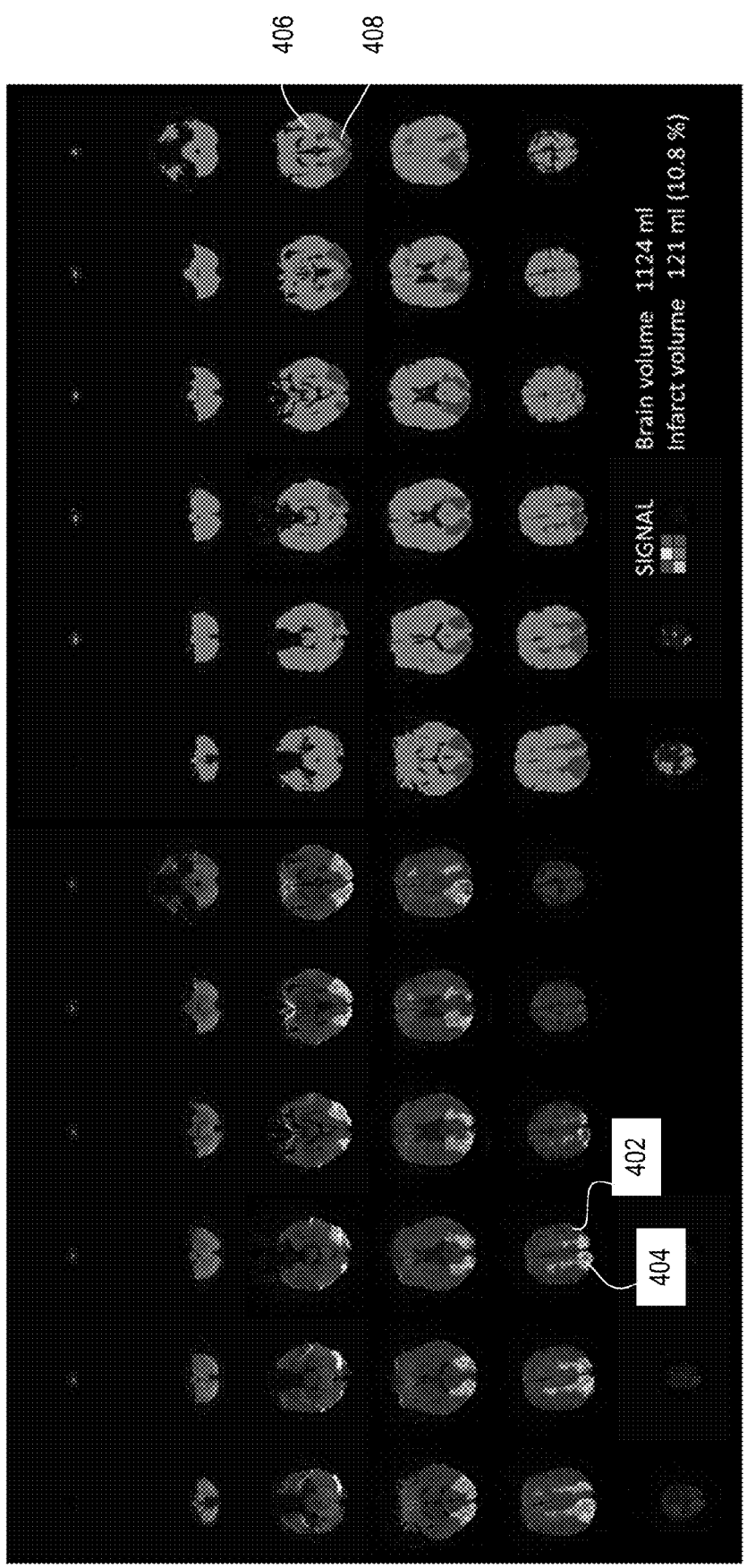
FIG. 4 depicts example results of AI-based measurement of relative infarct burden in a patient's brain.

FIG. 4 depicts example results of AI-based measurement of relative infarct burden in a patient's brain. Image data 400 depicts the AI-based measurement of relative infarct burden. Diffusion-weighted imaging (DWI) is used in the example of FIG. 4. DWI sequences represent both grey 402 and white 404 matter in a patient's brain. DWI shows little signal in cerebrospinal fluid (CSF), bone, muscle, fat, and connective tissue spaces. Thus, the DWI can be used for simple DWI-based brain volumetry determinations using the techniques described throughout. As discussed throughout this disclosure one or more other types of image data can also be used for brain volumetry determinations.

The computer system 104 can perform steps such as counting all voxels within predetermined DWI range or ranges in order to infer and calculate brain volume. Brain volume 406 can be represented in a first indicia, such as a green color. Here, the computer system 104 determined that the brain volume is 1,124 ml. Volumes of interest, or infarcted regions, that had been identified by the computer system 104 using the techniques described throughout this disclosure can be superimposed or overlaid on the brain volume 406. Infarcted regions 408 can be visually represented in a second indicia, such as a red color. The infarcted regions 408 can also be depicted in different indicia (e.g., different colors) depending on their identified volumes (not depicted in FIG. 4). The computer system 104 can infer the infarct volumes based on counting voxels in the infarcted regions 408. Here, the computer system 104 determined that the total infarct volume is 121 ml. The computer system 104 can then determine a ratio of voxels in a first indicia (e.g., a red color) to voxels in a second indicia (e.g., a green color) in order to determine a relative infarct burden in terms of percent of total brain volume. The voxels in the first indicia can represent identified infarcts. The voxels in the second indicia can represent a total brain volume (e.g., grey matter). Accordingly, in the example of FIG. 4, the computer system 104 determines that the relative infarct burden is 10.8% (the ratio of red-colored or tinted voxels, representative of infarcts, to green-colored or tinted voxels, representative of brain volume). This information can be visually presented to a user, such as a clinician or other medical professional, and used to make more accurate decisions about the patient's condition, including their diagnosis and treatment.

Figure 5:
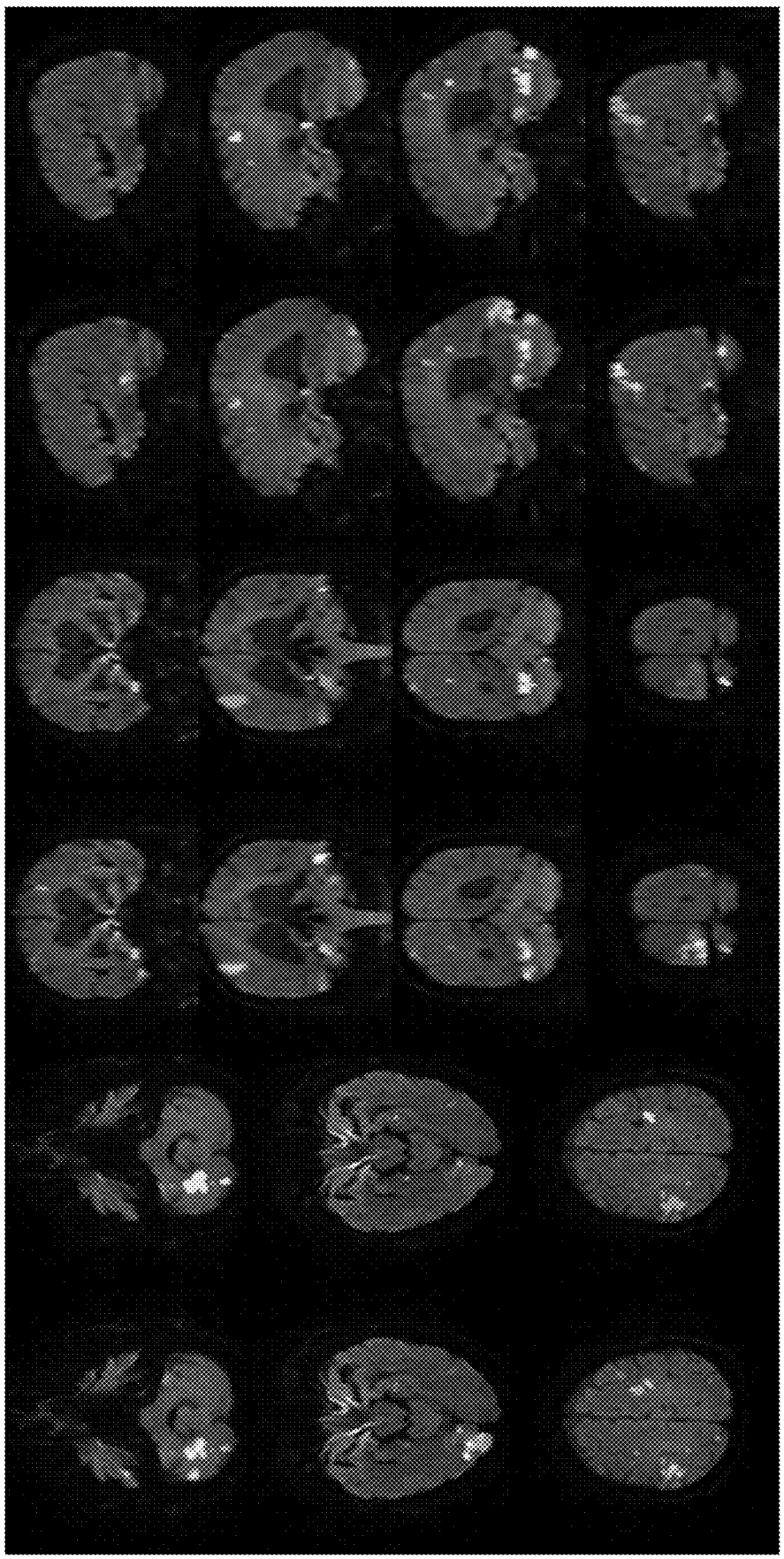
FIG. 5 depicts example AI-based coronal and sagittal views of detected infarcts in a patient's brain.

FIG. 5 depicts example AI-based coronal and sagittal views of detected infarcts in a patient's brain. Image data 500 depicts the AI-based coronal and sagittal views of the detected infarcts. As described above, different infarct volumes are depicted in different indicia or colors based on their volumes. The color sequence used in FIG. 5 is red-orange-yellow-green-blue-purple. Red indicates a largest identified infarct volume while purple indicates a smallest identified infarct volume. Each of the remaining colors (orange, yellow, green, and blue) can be used to indicate varying ranges of identified infarct volume. One or more other color sequences or indicia (e.g., patterns, other textures) can be used to visually represent the different infarct volumes in a patient's brain.

Here, the DWI stacks from FIG. 3 are permuted, by the computer system 104, into virtual sagittal and coronal slices (e.g., views). Such slices can provide a user with additional views for more accurately analyzing different portions of the patient's brain. Simultaneous review of the identified volumes of interest in axial, sagittal, and coronal orientations can provide some advantages to the user. For example, the different views can result in higher confidence in accepting or verifying certain volumes of interest as ischemic infarcts or rejecting them as non-infarct volumes. This can lead to more accurate diagnoses and treatments. As another example, the different views provide for improved and more accurate inferences of a suspected stroke etiology for the particular patient (e.g., embolic, watershed, lacunar). Therefore, more accurate determinations can be made with regards to diagnosis and treating a patient as well as predicting health-related repercussions that the patient may experience due to their identified stroke event.

Figure 6:
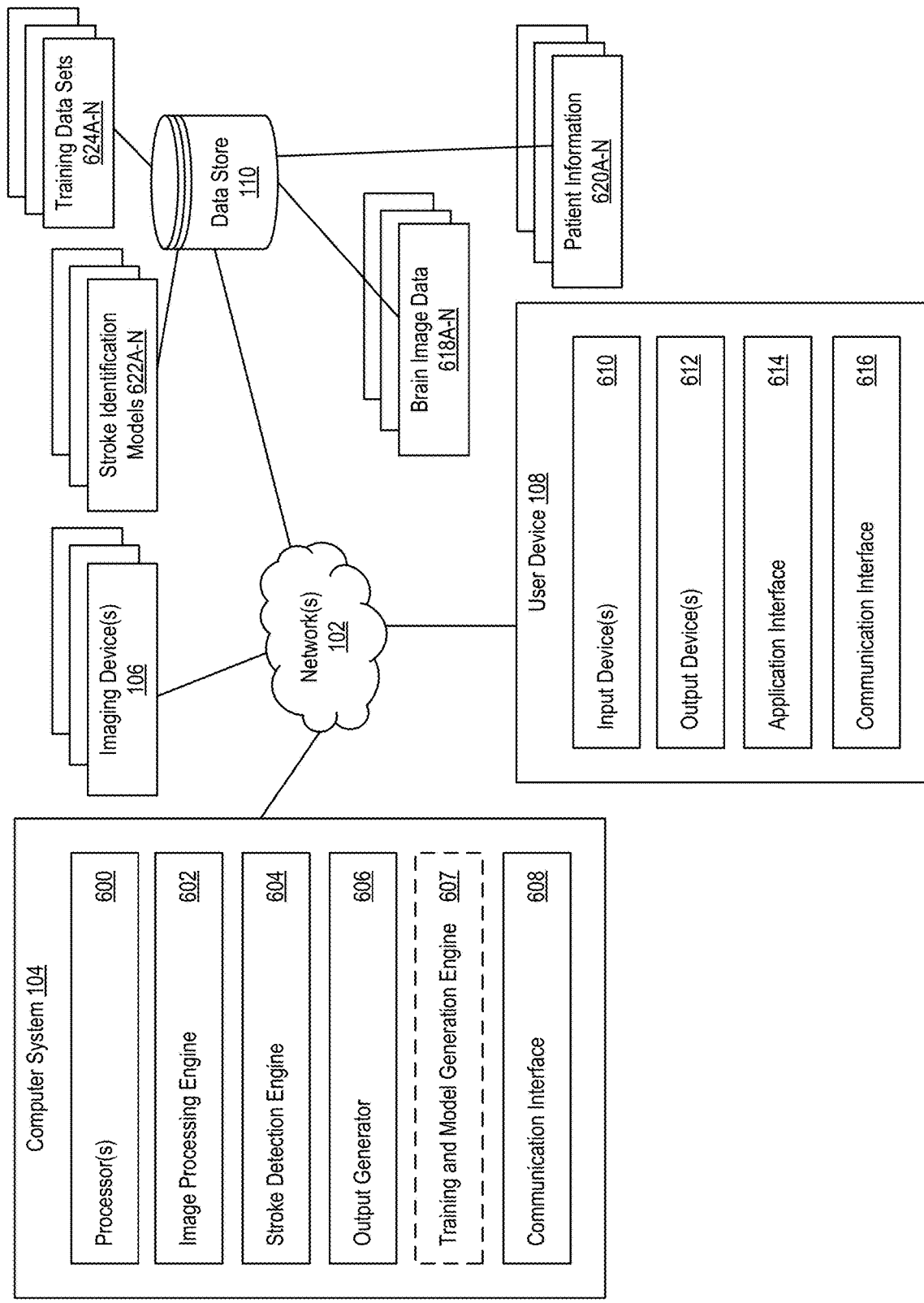
FIG. 6 is a system diagram of example computer components that can be used for performing the techniques described herein.

FIG. 6 is a system diagram of example computer components that can be used for performing the techniques described herein. The computer system 104, imaging device(s) 106, user device 108, and data store 110 can communicate via the network(s) 102. Moreover, one or more of the computer system 104, imaging device(s) 106, user device 108, and data store 110 can be integrated or otherwise part of a same computer system, network, and/or cloud-based service.

The imaging device(s) 106 can be configured to capture images of a subject's brain. The imaging device(s) 106 can be any type of device for imaging the brain, as described throughout this disclosure. Example imaging device(s) 106 include but are not limited to CT scans, MRIs, and x-rays. Other imaging devices are also possible. Images captured by the imaging device(s) 106 can be transmitted to the computer system 104 for processing and analysis, the user device 108 for viewing and analysis, and/or the data store 110 for storage and future retrieval.

The data store 110 can store information that is used by the computer system 104 to process and analyze the brain image data. In some implementations, the information can stored across multiple data stores, databases, repositories, and/or cloud-based storage. The data store 110 can store information such as brain image data 618A-N, patient information 620A-N, stroke identification models 622A-N, and training data sets 624A-N.

The brain image data 618A-N can include images that are captured by the imaging device(s) 106. In some implementations, the brain image data 618A-N can first be processed to remove personally identifying information, thereby preserving patient privacy and complying with health privacy policies. The brain image data 618A-N can then be stored in the data store 110.

The patient information 620A-N can include health records about patients whose brains are imaged. The patient information 620A-N can be linked to the brain image data 618A-N. The patient information 620A-N can also include determinations made by the computer system 104. For example, if the computer system 104 identifies a stroke event in the brain image data 618A-N, the computer system 104 can generate an indication that a stroke event is detected, and then can store that indication in the corresponding patient information 620A-N. In some implementations, the patient information 620A-N can also include information that is inputted by a clinician or other relevant stakeholder at the user device 108. For example, if the clinician makes a diagnosis or prescribes some treatment (e.g., based on reviewing the brain image data 618A-N and/or output/determinations made by the computer system 104), the diagnosis or prescription can be inputted by the clinician at the user device 108 and stored in the corresponding patient information 620A-N in the data store 110. The patient information 620A-N can be accessed by the user device 108, the computer system 104, and/or other systems and/or devices that are in secure communication with the data store 110 or part of a same healthcare infrastructure.

The stroke identification models 622A-N can be machine learning models used by the computer system 104 to analyze the brain image data 618A-N. Thus, the computer system 104 can use one or more of the models 622A-N to determine whether stroke events are present in the brain image data 618A-N. For example, the models 622A-N can be trained to identify volumes of interest in the brain image data 618A-N, where such volumes of interest are indicative of stroke events. One or more of the models 622A-N can also be trained to determine brain volume, infarct volume, and relative infarct burden on the brain volume using the brain image data 618A-N. The models 622A-N can be trained to perform different functions/operations. For example, one or more of the models 622A-N can be trained and used to process the brain image data 618A-N. One or more of the models 622A-N can be trained and used to identify volumes of interest in the brain image data 618A-N. One or more of the models 622A-N can be trained and used to make determinations about whether the identified volumes of interest are indicative of stroke events. One or more of the models 622A-N can also be trained to generate coronal and sagittal views of detected volumes of interest in the brain image data 618A-N.

In some implementations, one or more of the models 622A-N can be trained to identify different types of infarcts and/or volumes of interest that are related to different types of strokes. For example, one or more of the models 622A-N can be trained and used to identify watershed infarcts while one or more other models are trained and used to identify embolic infarcts. The models 622A-N can be trained by the computer system 104 (or another computing system) using the training data sets 624A-N.

The training data sets 624A-N can comprise large data sets of training samples. The training samples can be brain image data, such as the brain image data 618A-N. Some of the training samples can be brain image data where stroke events were detected or identified. Some of the training samples can be brain image data of subjects who experienced strokes before or after the brain image data was captured. Some of the training samples can also be brain image data where stroke events were not detected or identified. In other words, some of the training samples can be brain image data of normal subjects, or subjects without any brain conditions indicative of stroke.

The training data sets 624A-N can indicate, for each training sample, whether the sample contains volumes of interest that are indicative of stroke events. Each of the training samples can be labeled with types of volumes of interest, quantities of each volume of interest, and an indication of whether the training sample has one or more stroke events. The training samples can be automatically labeled (e.g., by the computer system 104 or another computing system). The training samples can also be manually annotated and labeled by a clinician, medical professional, or other relevant stakeholder.

The computer system 104 can be configured to perform the techniques described herein, such as processing and analyzing the brain image data 618A-N to identify stroke events. The computer system 104 include processor(s) 600, image processing engine 602, stroke detection engine 604, output generator 606, training and model generation engine 607, and communication interface 608. In some implementations, one or more components of the computer system 104 can be part of other computer systems, networks, devices, and/or cloud-based services.

The processor(s) 600 can be configured to execute instructions to perform the techniques described throughout this disclosure. The image processing engine 602 can be configured to process the brain image data 618A-N. For example, the engine 602 can receive the raw brain image data 618A-N from the imaging device(s) 106, the data store 110, and/or the user device 108. The engine 602 can process the received image data 618A-N to remove header data and/or personally identifying information. The engine 602 can store the processed brain image data in the data store 110. In some implementations, the image processing engine 602 can employ one or more machine learning models (e.g., one or more of the stroke identification models 622A-N) to process the brain image data 618A-N.

The stroke detection engine 604 can use the processed brain image data to determine whether the brain image data depicts volumes of interest indicative of stroke events. In some implementations, the stroke detection engine 604 can retrieve the stroke identification models 622A-N from the data store 110. The engine 604 can apply those models 622A-N to identify stroke events in the brain image data 618A-N. For example, the stroke detection engine 604 can provide the processed brain image data as input to one or more of the models 622A-N. The models 622A-N can output information such as whether stroke events are detected, what volumes of interest are identified in the brain image data, a volume of the brain, a visual representation of the volumes of interest overlaying the brain image data, a relative infarct burden on the total brain volume, a severity of the detected stroke events, a prediction of whether the subject is likely to develop stroke events, a prediction of what side effects/ cognitive impairments the subject may experience, and/or suggestions for diagnosis and treatment. Output from the models 622A-N can be stored in the data store 110 in the patient information 620A-N. Output from the models 622A-N can also be used by the output generator 606.

The output generator 606 can be configured to generate information that can be presented to a user at the user device 108. The output generator 606 can, for example, generate GUIs and other visual representations of the brain image data 718A-N with overlaid volumes of interest. The output generator 606 can also generate notifications, alerts, messages, alarms, or other information that can be presented at the user device 108 to notify the relevant user of an identified stroke event, severity score, risk prediction of developing stroke, and/or prediction of cognitive or other health impairments that may result from the identified stroke event. The output generator 606 can transmit output directly to the user device 108 for display. The output generator 606 can also store the output in the data store 110, for example as part of the patient information 620A-N.

The training and model generation engine 607 can be optional. The engine 607 can be configured to train the stroke identification models 622A-N. The engine 607 can retrieve the training data sets 624A-N and use those to generate and train the models 622A-N. Training and model generation can be performed before runtime. During runtime, the engine 607 can continuously improve the models 622A-N based on determinations that are made by the image processing engine 602 and/or the stroke detection engine 604. Over time, the models 622A-N can more accurately detect stroke events and other information from the brain image data 618A-N. In some implementations, the training and model generation engine 607 can be part of a different, remote computer system.

The communication interface 608 can provide for communication between the components described herein.

As described herein, the user device 108 can be used by a clinician, medical professional, or other relevant stakeholder. The user device 108 can be any one of a computer, tablet, laptop, mobile phone, smart phone, and/or cellphone. In some implementations, the user device 108 can be integrated with or part of the imaging device(s) 106 and/or the computer system 104. Moreover, the user device 108 can be remote from one or more of the components described herein. For example, the imaging device 106 can be locate at a clinic and the user device 108 can be a clinician's mobile phone that is remote from the clinic where a subject's brain is being imaged. Once the brain is imaged by the imaging device 106 at the clinic, the imaging device 106 can transmit the image data to the user device 108 over a secure communication/network, even though the user device 108 is remote from the clinic. The clinician, regardless of where they are located, can therefore review the brain image data and any processing/analysis performed by the computer system 104 at the user device 108. The user device 108 can include input device(s) 610, output device(s) 612, application interface 614, and communication interface 616.

The input device(s) 610 can be configured to receive input from a clinician or other user. The input device(s) 610 can include a touch screen, mouse, keyboard, microphone, display, or other device for receiving input.

The output device(s) 612 can be configured to present information at the user device 108 to the clinician or other user. The output device(s) 612 can include a touch screen, speaker, display screen, or other audio or visual display for outputting information.

The application interface 614 can be configured to present an application, software, or other program at the user device 108 for interacting with the imaging device(s) 106, the data store 110, and the computer system 104. For example, an application program can be installed at the user device 108 and executed via the application interface 614. The application program can allow for the user to view the brain image data 618A-N and to view and interact with output that is generated by the computer system 104. For example, the stroke detection engine 604 of the computer system 104 can identify volumes of interest in a particular subject's brain. The output generator 606 can generate a visual representation of the subject's brain image data with the identified volumes of interest overlaid thereon. This visual representation can be transmitted to the user device 108 and provided to the user via the application interface 614. The user can then select different views of the brain image data (e.g., coronal or sagittal views) by interacting with the visual representation of the brain image data. This input can be transmitted to the computer system 104 such that the output generator 606 of the computer system 104 can update the visual representation of the brain image data.

The communication interface 616 can provide for communication between the components described herein.

FIG. 7 shows a diagram of an exemplary computer processing system that can execute the techniques described herein. Computing device 700 is intended to represent various forms of digital computers, such as laptops, desktops, workstations, personal digital assistants, servers, blade servers, mainframes, and other appropriate computers. The mobile computing device is intended to represent various forms of mobile devices, such as personal digital assistants, cellular telephones, smart-phones, and other similar computing devices. The components shown here, their connections and relationships, and their functions, are meant to be exemplary only, and are not meant to limit implementations of the inventions described and/or claimed in this document.

The computing device 700 includes a processor 702, a memory 704, a storage device 706, a high-speed interface 708 connecting to the memory 704 and multiple high-speed expansion ports 710, and a low-speed interface 712 connecting to a low-speed expansion port 714 and the storage device 706. Each of the processor 702, the memory 704, the storage device 706, the high-speed interface 708, the high-speed expansion ports 710, and the low-speed interface 712, are interconnected using various busses, and can be mounted on a common motherboard or in other manners as appropriate. The processor 702 can process instructions for execution within the computing device 700, including instructions stored in the memory 704 or on the storage device 706 to display graphical information for a GUI on an external input/output device, such as a display 716 coupled to the high-speed interface 708. In other implementations, multiple processors and/or multiple buses can be used, as appropriate, along with multiple memories and types of memory. Also, multiple computing devices can be connected, with each device providing portions of the necessary operations (e.g., as a server bank, a group of blade servers, or a multi-processor system).

The memory 704 stores information within the computing device 700. In some implementations, the memory 704 is a volatile memory unit or units. In some implementations, the memory 704 is a non-volatile memory unit or units. The memory 704 can also be another form of computer-readable medium, such as a magnetic or optical disk.

The storage device 706 is capable of providing mass storage for the computing device 700. In some implementations, the storage device 706 can be or contain a computer-readable medium, such as a floppy disk device, a hard disk device, an optical disk device, or a tape device, a flash memory or other similar solid state memory device, or an array of devices, including devices in a storage area network or other configurations. A computer program product can be tangibly embodied in an information carrier. The computer program product can also contain instructions that, when executed, perform one or more methods, such as those described above. The computer program product can also be tangibly embodied in a computer- or machine-readable medium, such as the memory 704, the storage device 706, or memory on the processor 702.

The high-speed interface 708 manages bandwidth-intensive operations for the computing device 700, while the low-speed interface 712 manages lower bandwidth-intensive operations. Such allocation of functions is exemplary only. In some implementations, the high-speed interface 708 is coupled to the memory 704, the display 716 (e.g., through a graphics processor or accelerator), and to the high-speed expansion ports 710, which can accept various expansion cards (not shown). In the implementation, the low-speed interface 712 is coupled to the storage device 706 and the low-speed expansion port 714. The low-speed expansion port 714, which can include various communication ports (e.g., USB, Bluetooth, Ethernet, wireless Ethernet) can be coupled to one or more input/output devices, such as a keyboard, a pointing device, a scanner, or a networking device such as a switch or router, e.g., through a network adapter.

The computing device 700 can be implemented in a number of different forms, as shown in the figure. For example, it can be implemented as a standard server 720, or multiple times in a group of such servers. In addition, it can be implemented in a personal computer such as a laptop computer 722. It can also be implemented as part of a rack server system 724. Alternatively, components from the computing device 700 can be combined with other components in a mobile device (not shown), such as a mobile computing device 750. Each of such devices can contain one or more of the computing device 700 and the mobile computing device 750, and an entire system can be made up of multiple computing devices communicating with each other.

The mobile computing device 750 includes a processor 752, a memory 764, an input/output device such as a display 754, a communication interface 766, and a transceiver 768, among other components. The mobile computing device 750 can also be provided with a storage device, such as a micro-drive or other device, to provide additional storage. Each of the processor 752, the memory 764, the display 754, the communication interface 766, and the transceiver 768, are interconnected using various buses, and several of the components can be mounted on a common motherboard or in other manners as appropriate.

The processor 752 can execute instructions within the mobile computing device 750, including instructions stored in the memory 764. The processor 752 can be implemented as a chipset of chips that include separate and multiple analog and digital processors. The processor 752 can provide, for example, for coordination of the other components of the mobile computing device 750, such as control of user interfaces, applications run by the mobile computing device 750, and wireless communication by the mobile computing device 750.

The processor 752 can communicate with a user through a control interface 758 and a display interface 756 coupled to the display 754. The display 754 can be, for example, a TFT (Thin-Film-Transistor Liquid Crystal Display) display or an OLED (Organic Light Emitting Diode) display, or other appropriate display technology. The display interface 756 can comprise appropriate circuitry for driving the display 754 to present graphical and other information to a user. The control interface 758 can receive commands from a user and convert them for submission to the processor 752. In addition, an external interface 762 can provide communication with the processor 752, so as to enable near area communication of the mobile computing device 750 with other devices. The external interface 762 can provide, for example, for wired communication in some implementations, or for wireless communication in other implementations, and multiple interfaces can also be used.

The memory 764 stores information within the mobile computing device 750. The memory 764 can be implemented as one or more of a computer-readable medium or media, a volatile memory unit or units, or a non-volatile memory unit or units. An expansion memory 774 can also be provided and connected to the mobile computing device 750 through an expansion interface 772, which can include, for example, a SIMM (Single In Line Memory Module) card interface. The expansion memory 774 can provide extra storage space for the mobile computing device 750, or can also store applications or other information for the mobile computing device 750. Specifically, the expansion memory 774 can include instructions to carry out or supplement the processes described above, and can include secure information also. Thus, for example, the expansion memory 774 can be provide as a security module for the mobile computing device 750, and can be programmed with instructions that permit secure use of the mobile computing device 750. In addition, secure applications can be provided via the SIMM cards, along with additional information, such as placing identifying information on the SIMM card in a non-hackable manner.

The memory can include, for example, flash memory and/or NVRAM memory (non-volatile random access memory), as discussed below. In some implementations, a computer program product is tangibly embodied in an information carrier. The computer program product contains instructions that, when executed, perform one or more methods, such as those described above. The computer program product can be a computer- or machine-readable medium, such as the memory 764, the expansion memory 774, or memory on the processor 752. In some implementations, the computer program product can be received in a propagated signal, for example, over the transceiver 768 or the external interface 762.

The mobile computing device 750 can communicate wirelessly through the communication interface 766, which can include digital signal processing circuitry where necessary. The communication interface 766 can provide for communications under various modes or protocols, such as GSM voice calls (Global System for Mobile communications), SMS (Short Message Service), EMS (Enhanced Messaging Service), or MMS messaging (Multimedia Messaging Service), CDMA (code division multiple access), TDMA (time division multiple access), PDC (Personal Digital Cellular), WCDMA (Wideband Code Division Multiple Access), CDMA2000, or GPRS (General Packet Radio Service), among others. Such communication can occur, for example, through the transceiver 768 using a radio-frequency. In addition, short-range communication can occur, such as using a Bluetooth, WiFi, or other such transceiver (not shown). In addition, a GPS (Global Positioning System) receiver module 770 can provide additional navigation- and location-related wireless data to the mobile computing device 750, which can be used as appropriate by applications running on the mobile computing device 750.

The mobile computing device 750 can also communicate audibly using an audio codec 760, which can receive spoken information from a user and convert it to usable digital information. The audio codec 760 can likewise generate audible sound for a user, such as through a speaker, e.g., in a handset of the mobile computing device 750. Such sound can include sound from voice telephone calls, can include recorded sound (e.g., voice messages, music files, etc.) and can also include sound generated by applications operating on the mobile computing device 750.

The mobile computing device 750 can be implemented in a number of different forms, as shown in the figure. For example, it can be implemented as a cellular telephone 7870. It can also be implemented as part of a smart-phone 7872, personal digital assistant, or other similar mobile device.

Various implementations of the systems and techniques described here can be realized in digital electronic circuitry, integrated circuitry, specially designed ASICs (application specific integrated circuits), computer hardware, firmware, software, and/or combinations thereof. These various implementations can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device.

These computer programs (also known as programs, software, software applications or code) include machine instructions for a programmable processor, and can be implemented in a high-level procedural and/or object-oriented programming language, and/or in assembly/machine language. As used herein, the terms machine-readable medium and computer-readable medium refer to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term machine-readable signal refers to any signal used to provide machine instructions and/or data to a programmable processor.

To provide for interaction with a user, the systems and techniques described here can be implemented on a computer having a display device (e.g., a CRT (cathode ray tube) or LCD (liquid crystal display) monitor) for displaying information to the user and a keyboard and a pointing device (e.g., a mouse or a trackball) by which the user can provide input to the computer. Other kinds of devices can be used to provide for interaction with a user as well; for example, feedback provided to the user can be any form of sensory feedback (e.g., visual feedback, auditory feedback, or tactile feedback); and input from the user can be received in any form, including acoustic, speech, or tactile input.

The systems and techniques described here can be implemented in a computing system that includes a back end component (e.g., as a data server), or that includes a middleware component (e.g., an application server), or that includes a front end component (e.g., a client computer having a graphical user interface or a Web browser through which a user can interact with an implementation of the systems and techniques described here), or any combination of such back end, middleware, or front end components. The components of the system can be interconnected by any form or medium of digital data communication (e.g., a communication network). Examples of communication networks include a local area network (LAN), a wide area network (WAN), and the Internet.

The computing system can include clients and servers. A client and server are generally remote from each other and typically interact through a communication network. The relationship of client and server arises by virtue of computer programs running on the respective computers and having a client-server relationship to each other.

While this specification contains many specific implementation details, these should not be construed as limitations on the scope of the disclosed technology or of what may be claimed, but rather as descriptions of features that may be specific to particular embodiments of particular disclosed technologies. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination. Similarly, while operations may be described in a particular order, this should not be understood as requiring that such operations be performed in the particular order or in sequential order, or that all operations be performed, to achieve desirable results. Particular embodiments of the subject matter have been described. Other embodiments are within the scope of the following claims.

The invention claimed is:

1. A system for automated identification of volumes of interest in brain image data, the system comprising:
one or more processors; and
computer memory storing instructions that, when executed by the processors, cause the processors to perform operations comprising:
receiving image data of a brain having header data and voxel values, wherein the voxel values represent an interruption in blood supply of the brain when imaged;
extracting the header data from the image data;
populating an array of cells with the voxel values;
applying a segmenting analysis to the array to generate a segmented array;
applying a morphological neighborhood analysis to the segmented array to generate a features relationship array, wherein the features relationship array includes features of interest in the brain indicative of stroke;
identifying three-dimensional (3D) connected volumes of interest in the features relationship array; and
generating output, for display at a user device, indicating the identified 3D volumes of interest.

2. The system of claim 1, wherein the 3D volumes of interest are at least one of watershed infarcts and embolic infarcts in the brain indicative of ischemic stroke.

3. The system of claim 1, wherein the image data of the brain is generated by at least one of computed tomography (CT) and Magnetic Resonance Imaging (MRI).

4. The system of claim 1, wherein the image data of the brain includes time-series data of the brain.

5. The system of claim 1, wherein the operations further comprise applying a filtering analysis to the array to generate a filtered array based on:
identifying a subset of the cells in the array to exclude from the filtered array; and
removing the identified subset of the cells to generate the filtered array.

6. The system of claim 1, wherein applying the segmenting analysis comprises segmenting the cells of the array based on physiological structures of the brain.

7. The system of claim 1, wherein applying the morphological neighborhood analysis comprises identifying features of interest in the segmented array based on connectivity data amongst the cells in the segmented array.

8. The system of claim 1, wherein the operations further comprise storing, in a data store, the identified 3D volumes of interest.

9. The system of claim 1, wherein identifying three dimensional (3D) connected volumes of interest comprises:
counting voxel values within a predefined region of the image data to infer a volume of the brain;
superimposing the identified 3D volumes of interest on the within the predefined region of the image data; and
identifying relative infarct burden in percent of brain volume based on determining a ratio between the superimposed 3D volumes of interest and the inferred volume of the brain.

10. The system of claim 1, wherein generating output comprises generating coronal and sagittal views of the 3D volumes of interest in the brain image data.

11. The system of claim 1, wherein generating output comprises:
superimposing the 3D volumes of interest on the brain image data; and
tinting the 3D volumes of interest in one or more indicia that is different than an indicia of the brain image data.

12. The system of claim 11, wherein tinting the 3D volumes of interest comprises:
tinting a first of the 3D volumes of interest in a first indicia based on determining that a volume of the first of the 3D volumes of interest is greater than a first threshold level; and
tinting a second of the 3D volumes of interest in a second indicia based on determining that a volume of the second of the 3D volumes of interest is less than the first threshold level but greater than a second threshold level.

13. The system of claim 1, wherein identifying three-dimensional (3D) connected volumes of interest in the features relationship array is based on applying one or more machine learning models that were trained using training datasets that include training brain image data labeled with areas of interest and training brain image data labeled with areas that are not of interest.

14. A method for automatically identifying volumes of interest in brain image data, the method comprising:
receiving, by a computing system, image data of a brain having header data and voxel values, wherein the voxel values represent an interruption in blood supply of the brain when imaged;
extracting, by the computing system, the header data from the image data;
populating, by the computing system, an array of cells with the voxel values;
applying, by the computing system, a segmenting analysis to the array to generate a segmented array;
applying, by the computing system, a morphological neighborhood analysis to the segmented array to generate a features relationship array, wherein the features relationship array includes features of interest in the brain indicative of stroke;
identifying, by the computing system, three-dimensional (3D) connected volumes of interest in the features relationship array; and
generating, by the computing system and for display at a user device, output indicating the identified 3D volumes of interest.

15. The method of claim 14, further comprising applying, by the computing system, a filtering analysis to the array to generate a filtered array based on:
identifying a subset of the cells in the array to exclude from the filtered array; and
removing the identified subset of the cells to generate the filtered array.

16. The method of claim 14, wherein applying, by the computing system, the segmenting analysis comprises segmenting the cells of the array based on physiological structures of the brain.

17. The method of claim 14, wherein applying, by the computing system, the morphological neighborhood analysis comprises identifying features of interest in the segmented array based on connectivity data amongst the cells in the segmented array.

18. The method of claim 14, further comprising storing, by the computing system and in a data store, the identified 3D volumes of interest.

19. The method of claim 14, wherein identifying, by the computing system, three dimensional (3D) connected volumes of interest comprises:
counting voxel values within a predefined region of the image data to infer a volume of the brain;

superimposing the identified 3D volumes of interest on the within the predefined region of the image data; and identifying relative infarct burden in percent of brain volume based on determining a ratio between the superimposed 3D volumes of interest and the inferred volume of the brain.

20. The method of claim 14, wherein generating, by the computing system, output comprises generating coronal and sagittal views of the 3D volumes of interest in the brain image data.

* * * * *